(12) United States Patent
Fritzsche et al.

(10) Patent No.: US 8,262,949 B2
(45) Date of Patent: Sep. 11, 2012

(54) LONG WAVELENGTH SHIFTED BENZOTRIAZOLE UV-ABSORBERS AND THEIR USE

(75) Inventors: Katharina Fritzsche, Weil am Rhein (DE); Markus Grob, Reinach (SE); Adalbert Braig, Binzen (DE); Ilona Marion Kienzle, Weil am Rhein (DE); Gérard Daniel Georges Vilain, Ebringen (DE)

(73) Assignee: BASF SE, Ludwigshafen (DE)

( * ) Notice: Subject to any disclaimer, the term of this patent is extended or adjusted under 35 U.S.C. 154(b) by 237 days.

(21) Appl. No.: 12/308,278

(22) PCT Filed: Jun. 18, 2007

(86) PCT No.: PCT/EP2007/056004
§ 371 (c)(1),
(2), (4) Date: Dec. 11, 2008

(87) PCT Pub. No.: WO2008/000646
PCT Pub. Date: Jan. 3, 2008

(65) Prior Publication Data
US 2010/0163813 A1 Jul. 1, 2010

(30) Foreign Application Priority Data
Jun. 27, 2006 (EP) .................................... 06116114

(51) Int. Cl.
| | |
|---|---|
| *F21V 9/04* | (2006.01) |
| *F21V 9/06* | (2006.01) |
| *G02B 5/22* | (2006.01) |
| *G02B 5/26* | (2006.01) |
| *C09K 15/04* | (2006.01) |
| *C09K 15/32* | (2006.01) |
| *C09K 15/22* | (2006.01) |
| *C09K 15/16* | (2006.01) |
| *C07D 487/00* | (2006.01) |
| *C07D 249/16* | (2006.01) |
| *C07D 249/20* | (2006.01) |
| *C07D 403/00* | (2006.01) |

(52) U.S. Cl. ........ 252/589; 252/399; 252/401; 252/403; 252/404; 252/405; 544/251; 544/345; 546/82; 548/151; 548/218; 548/256; 548/257; 548/259

(58) Field of Classification Search .................. 252/589, 252/403, 399, 401, 404, 405; 544/251, 345; 546/82; 548/151, 218, 259, 256, 257
See application file for complete search history.

(56) References Cited

U.S. PATENT DOCUMENTS

| | | | |
|---|---|---|---|
| 5,436,349 A | 7/1995 | Winter et al. | ................. 548/259 |
| 6,166,218 A | 12/2000 | Ravichandran et al. | ...... 548/257 |
| 6,835,329 B2 | 12/2004 | Reinehr et al. | ................ 252/401 |
| 2008/0157025 A1* | 7/2008 | Fritzsche et al. | .............. 252/403 |

FOREIGN PATENT DOCUMENTS

| | | |
|---|---|---|
| EP | 0 717 313 | 6/1996 |
| WO | 02/28854 | 4/2002 |

OTHER PUBLICATIONS

Keto-enol tautomerism—Wikipedia, the free encyclopedia, http://en.wikipedia.org/wiki/Keto-enol_tautomerism, dated Nov. 13, 2010.*

* cited by examiner

*Primary Examiner* — Bijan Ahvazi
(74) *Attorney, Agent, or Firm* — Shruti Costales

(57) ABSTRACT

The instant invention relates to novel benzotriazole UV-absorbers having a long wavelength shifted absorption spectrum with significant absorbance up to 410-420 nm. Further aspects of the invention are a process for their preparation, a UV stabilized composition containing the new UV-absorbers and the use of the new compounds as UV-light stabilizers for organic materials.

22 Claims, No Drawings

LONG WAVELENGTH SHIFTED BENZOTRIAZOLE UV-ABSORBERS AND THEIR USE

The instant invention relates to novel benzotriazole UV-absorbers having a long wavelength shifted absorption spectrum with significant absorbance up to 410-430 nm. Further aspects of the invention are a process for their preparation, a UV stabilized composition containing the new UV-absorbers and the use of the new compounds as UV-light stabilizers for organic materials.

Polymeric substrates containing aromatic moieties, such as for example adhesives or coating resins based on aromatic epoxides, aromatic polyesters or aromatic (poly-) isocyanates are highly sensitive to UV/VIS radiation up to wavelengths of approximately 410 to 420 nm.

The protection of such adhesive or coating layers with a UV absorbing layer on top is extremely difficult, since already very small amounts of radiation—even in the range of around 410 nm—penetrating the UV absorbing top coating are sufficient to cause delamination and peeling off of the protective coating.

Typical applications, in which long wavelength shifted UV absorbers are extremely useful, are automotive coatings, typically two coat metallic automotive coatings.

Today's automotive coatings have applied an anticorrosive cathodic electro coat directly on the steel plate. Due to the significantly red shifted light sensitivity of the cathodic resins (up to approximately 400-420 nm) it is not possible to protect the cathodic electro coat with conventional prior art UV-absorbers in the top coatings adequately.

In order to better protect such sensitive layers, attempts have been made to shift the UV absorption of benzotriazoles towards longer wavelengths. For example, U.S. Pat. No. 5,436,349 discloses benzotriazole UV-absorbers, which are substituted in the 5 position of the benzo ring by alkylsulfonyl groups. However, the absorption shift is not large enough to protect such highly sensitive materials.

U.S. Pat. No. 6,166,218 discloses, for example, benzotriazole UV-absorbers, which are substituted in the 5-position of the benzo ring with a $CF_3$ group, leading also to a slightly long wavelength shifted absorbance and to an enhanced photochemical stability. This absorption shift, however, is by far not large enough to protect materials with a photochemical sensitivity up to 410 nm.

Surprisingly it has now been found, that when the benzo ring of benzotriazole UV-absorbers is part of a heterocyclic system a large shift of the absorption maximum of approximately 20-40 nm is observed, extending up to 430 nm with a steep slope towards the visible region. The compounds show very high extinction coefficients and remain unexpectedly photochemically stable and show virtually no migration in typical coating applications.

One aspect of the instant invention is a compound of formula (I)

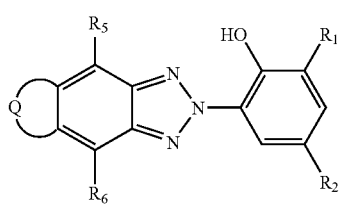

(I)

wherein
Q is a heterocyclic radical forming a 5 or 6-membered ring together with the annealed phenyl-ring, which radical is selected from the group consisting of

wherein
$X_{10}$ is O=C, S=C, $R_{101}N$, $S(O)_n$ where n is 0, 1 or 2;
$Y_{10}$ is $NR_{101}$, O, $S(O)_n$ where n is 0, 1 or 2;
$Z_{10}$ is O=C, S=C, $R_{101}N$, O, $S(O)_n$ where n is 0, 1 or 2;

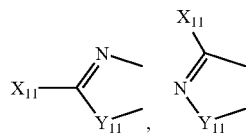

wherein
$X_{11}$ is $R_{101}$, $N(R_{101})_2$, $OR_{101}$, $S(O)_nR_{101}$ where n is 0, 1 or 2;
$Y_{11}$ is C=O, $NR_{101}$, O, or $S(O)_n$ where n is 0, 1 or 2;

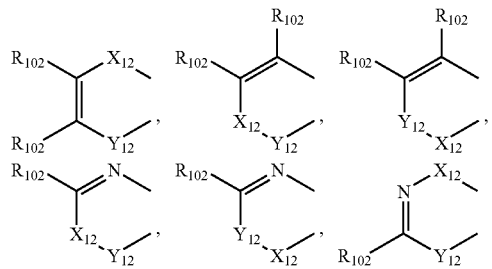

wherein
$X_{12}$ is C=O or C=S;
$Y_{12}$ is $NR_{101}$, O or S;

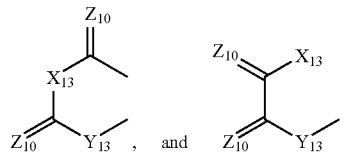

wherein
$X_{13}$ and $Y_{13}$ are independently $NR_{101}$, O or S;
the $Z_{10}$ are independently from each other O or S;
$R_{101}$ is hydrogen, straight or branched chain $C_1$-$C_{24}$alkyl, straight or branched chain $C_2$-$C_{18}$alkenyl, $C_2$-$C_6$alkinyl, $C_5$-$C_{12}$cycloalkyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more -halogen, —OH, —$OR_{22}$, —$NH_2$, —$NHR_{22}$, —$N(R_{22})_2$, —$NHCOR_{23}$, —$NR_{22}COR_{23}$, —$OCOR_{24}$, —$COR_{25}$, —$SO_2R_{26}$, —$SO_3$⁻M⁺, —$PO(R_{27})_n(R_{28})_{2-n}$, —$Si(R_{29})_n(R_{30})_{3-n}$, —$Si(R_{22})_3$, —N⁺$(R_{22})_3$A⁻, —S⁺$(R_{22})_2$A⁺ or combinations thereof; said straight or branched chain unsubstituted or substituted $C_1$-$C_{24}$ alkyl, straight or branched chain unsubstituted or substituted $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;

said phenyl, naphthyl or $C_7$-$C_{15}$-phenylalkyl can also be substituted by one or more -halogen, —CN, —$CF_3$, —$NO_2$, —$NHR_{22}$, —$N(R_{22})_2$, —$SO_2R_{26}$, —$PO(R_{27})_n$ $(R_{28})_{2-n}$, —OH, —$OR_{22}$, —$COR_{25}$, —$R_{25}$; wherein n is 0, 1 or 2;

$R_{22}$ is straight or branched chain $C_1$-$C_{18}$ alkyl, straight or branched chain $C_2$-$C_{18}$ alkenyl, $C_5$-$C_{10}$ cycloalkyl, phenyl or naphthyl, $C_7$-$C_{15}$ phenylalkyl, or two $R_{22}$ when attached to an N or Si atom can form together with the atom to which they are bonded a pyrrolidine, piperidine or morpholine ring;

$R_{23}$ is hydrogen, $OR_{22}$, $NHR_{22}$, $N(R_{22})_2$ or has the same meaning as $R_{22}$, $R_{24}$ is $OR_{22}$, $NHR_{22}$, $N(R_{22})_2$ or has the same meaning as $R_{22}$, $R_{25}$ is hydrogen, OH, $OR_{22}$, $NHR_{22}$ or $N(R_{22})_2$, or has the same meaning as $R_{22}$.

$R_{26}$ is OH, $OR_{22}$, $NHR_{22}$ or $N(R_{22})_2$, $R_{27}$ is $NH_2$, $NHR_{22}$ or $N(R_{22})_2$, $R_{28}$ is OH or $OR_{22}$, $R_{26}$ is Cl or $OR_{22}$, $R_{30}$ is straight or branched chain $C_1$-$C_{18}$ alkyl; or $R_{101}$ can be a bridging group of straight or branched $C_1$-$C_{18}$alkylene, $C_5$-$C_{10}$cycloalkylene, para-phenylene or a group

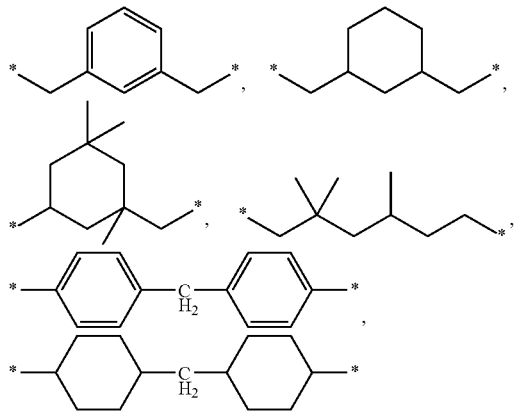

wherein * denotes a bond where the bridge connects two compounds of formula I, said $C_1$-$C_{12}$alkylene, $C_5$-$C_{10}$cycloalkylene can also be interrupted by one or more —O—, —S—, —NH— or —$NR_{22}$— groups or combinations thereof;

or when Y is a direct bond, Z can additionally also be a direct bond;

$R_{102}$ is hydrogen, —CN, —$COR_{24}$ straight or branched chain $C_1$-$C_{24}$alkyl, straight or branched chain $C_2$-$C_{18}$alkenyl, $C_2$-$C_6$alkinyl, $C_5$-$C_{12}$cycloalkyl, phenyl, naphthyl or $C_7$-$C_{15}$phenylalkyl; or if two substituents $R_{101}/R_{101}$, $R_{101}/R_{102}$ or $R_{102}/R_{102}$ are in vicinal position, they can form together with the atoms to which they are bonded an aliphatic, 5 to 8-membered ring;

$R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_1$ is a group

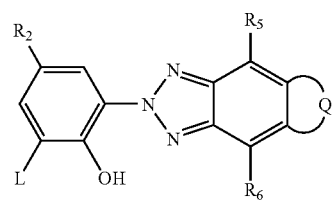

wherein

L is alkylene of 1 to 12 carbon atoms, alkylidene of 2 to 12 carbon atoms, benzylidene, p-xylylene or cycloalkylene of 5 to 7 carbon atoms;

$R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or said alkyl substituted by one or more —OH, —OCO—$R_{11}$, —$OR_{14}$, —NCO or —$NH_2$ groups or mixtures thereof, or said alkyl or said alkenyl interrupted by one or more —O—, —NH— or —$NR_{14}$— groups or mixtures thereof and which can be unsubstituted or substituted by one or more —OH, —$OR_{14}$ or —$NH_2$ groups or mixtures thereof; where $R_{11}$ is hydrogen, straight or branched chain $C_1$-$C_{18}$alkyl, $C_5$-$C_{12}$cycloalkyl, straight or branched chain $C_3$-$C_8$alkenyl, phenyl, naphthyl or $C_7$-$C_{15}$phenylalkyl; and $R_{14}$ is hydrogen, straight or branched chain alkyl of 1 to 24 carbon atoms; or $R_2$ is —$OR_{14}$, a group —C(O)—O—$R_{14}$, —C(O)—$NHR_{14}$ or —C(O)—$NR_{14}R'_{14}$ wherein $R'_{14}$ has the same meaning as $R_{14}$; or $R_2$ is —$SR_{13}$, —$NHR_{13}$ or —$N(R_{13})_2$; or $R_2$ is —$(CH_2)_m$—CO—$X_1$—$(Z)_p$—Y—$R_{15}$ wherein $X_1$ is —O— or —$N(R_{16})$—, Y is —O— or —$N(R_{17})$— or a direct bond, Z is $C_2$-$C_{12}$-alkylene, $C_4$-$C_{12}$alkylene interrupted by one to three nitrogen atoms, oxygen atoms or a mixture thereof, or is $C_3$-$C_{12}$alkylene, butenylene, butynylene, cyclohexylene or phenylene, each of which may be additionally substituted by a hydroxyl group;

or a group

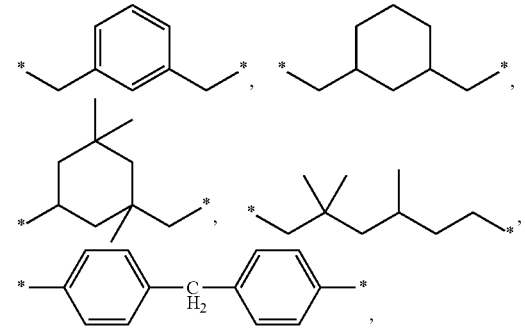

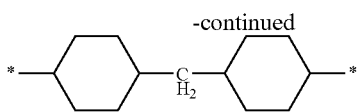

wherein * denotes a bond or when Y is a direct bond, Z can additionally also be a direct bond;

m is zero, 1 or 2, p is 1, or p is also zero when X and Y are —N(R$_{16}$)— and —N(R$_{17}$)—, respectively, R$_{15}$ is hydrogen, C$_1$-C$_{12}$alkyl, a group

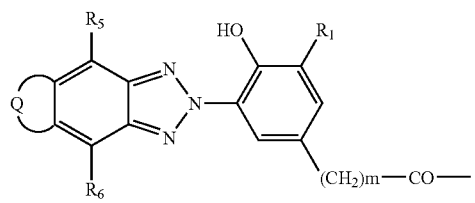

or a group —CO—C(R$_{18}$)=C(H)R$_{19}$ or, when Y is —N(R$_{17}$)—, forms together with R$_{17}$ a group —CO—CH=CH—CO— wherein R$_{18}$ is hydrogen or methyl, and R$_{19}$ is hydrogen, methyl or —CO—X$_1$—R$_{20}$, wherein R$_{20}$ is hydrogen, C$_1$-C$_{12}$alkyl or a group of formulae

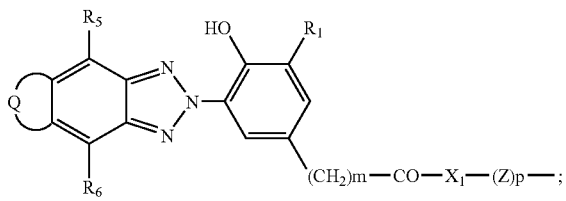

R$_5$ and R$_6$ are independently hydrogen or C$_1$-C$_{18}$alkylene;

R$_{13}$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, phenyl or naphthyl, which both may be substituted by one or two alkyl of 1 to 4 carbon atoms;

R$_{16}$ and R$_{17}$ independently of one another are hydrogen, C$_1$-C$_{12}$-alkyl, C$_3$-C$_{12}$-alkyl interrupted by 1 to 3 oxygen atoms, or is cyclohexyl or C$_7$-C$_{15}$phenylalkyl, and R$_{16}$ together with R$_{17}$ in the case where Z is ethylene, also forms ethylene.

In some cases tautomeric forms may exist. It is intended in the present invention to cover both tautomeric forms, although only one is explicitly outlined. An example is:

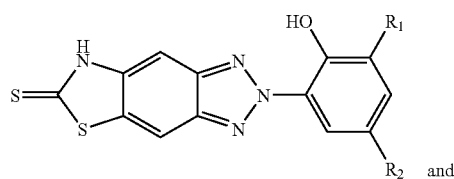

and

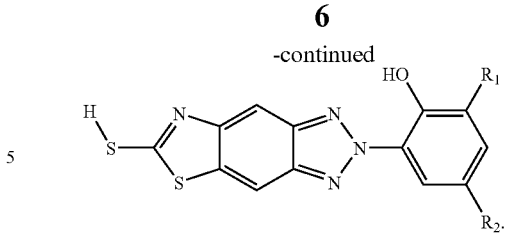

When any of the substituents are straight or branched chain alkyl of 1 to 24 carbon atoms, such groups are, for example, methyl, ethyl, isopropyl, n-butyl, isobutyl, sec-butyl, tert-butyl, tert-amyl, 2-ethylhexyl, tert-octyl, lauryl, tert-dodecyl, tridecyl, n-hexadecyl, n-octadecyl or eicosyl.

When any of said substituents are straight or branched chain alkenyl of 2 to 18 carbon atoms, such groups are, for example, allyl, pentenyl, hexenyl, doceneyl or oleyl. Preference is given to alkenyl having from 3 to 16, especially from 3 to 12, for example from 2 to 6, carbon atoms.

When any of said substituents are cycloalkyl of 5 to 12 carbon atoms, such groups are, for example, cyclopentyl, cyclohexyl, cycloheptyl, cyclooctyl and cyclododecyl. C$_1$-C$_4$alkyl-substituted C$_5$-C$_8$cycloalkyl is, for example, methylcyclopentyl, dimethylcyclopentyl, methylcyclohexyl, dimethylcyclohexyl, trimethylcyclohexyl or tert-butylcyclohexyl.

When any of said radicals are phenylalkyl of 7 to 15 carbon atoms, such groups are, for example, benzyl, phenethyl, α-methylbenzyl or α,α-dimethylbenzyl.

When phenyl is substituted by alkyl, this is, for example, tolyl and xylyl.

Alkyl substituted by one or more —O— groups and/or substituted by one or more —OH can, for example, be —(OCH$_2$CH$_2$)$_w$OH or —(OCH$_2$CH$_2$)$_w$O(C$_1$-C$_{24}$alkyl) where w is 1 to 12.

Alkyl interrupted by one or more —O— can be derived from ethyleneoxide units or from propyleneoxide units or from mixtures of both.

When alkyl is interrupted by —NH— or —NR$_{14}$— the radicals are derived in analogy to the above —O— interrupted radicals. Preferred are repeating units of ethylenediamine.

Examples are CH$_3$—O—CH$_2$CH$_2$—, CH$_3$—NH—CH$_2$CH$_2$—, CH$_3$—N(CH$_3$)—CH$_2$—, CH$_3$—O—CH$_2$CH$_2$—O—CH$_2$CH$_2$—, CH$_3$—(O—CH$_2$CH$_2$—)$_2$O—CH$_2$CH$_2$—, CH$_3$—(O—CH$_2$CH$_2$—)$_3$O—CH$_2$CH$_2$— or CH$_3$—(O—CH$_2$CH$_2$—)$_4$O—CH$_2$CH$_2$—.

Alkylene is, for example, ethylene, tetramethylene, hexamethylene, 2-methyl-1,4-tetramethylene, hexamethylene, octamethylene, decamethylene and dodecamethylene.

Cycloalkylene is, for example, cyclopentylene, cyclohexylene, cycloheptylene, cyclooctylene and cyclododecylene. Preference is given to cyclohexylene.

Alkylene interrupted by oxygen, NH or —NR$_{14}$— is, for example, —CH$_2$CH$_2$—O—CH$_2$CH$_2$—, —CH$_2$CH$_2$—NH—CH$_2$CH$_2$—, —CH$_2$CH$_2$—N(CH$_3$)—CH$_2$CH$_2$—, —CH$_2$CH$_2$—O—CH$_2$CH$_2$—O—CH$_2$CH$_2$—, —CH$_2$CH$_2$—(O—CH$_2$CH$_2$—)$_2$O—CH$_2$CH$_2$—, —CH$_2$CH$_2$—(O—CH$_2$CH$_2$—)$_3$O—CH$_2$CH$_2$—, —CH$_2$CH$_2$—(O—CH$_2$CH$_2$—)$_4$O—CH$_2$CH$_2$— or —CH$_2$CH$_2$—NH—CH$_2$CH$_2$—.

The radical Q is straight or branched $C_1$-$C_{12}$alkylene, $C_5$-$C_{10}$cycloalkylene, para-phenylene or a group

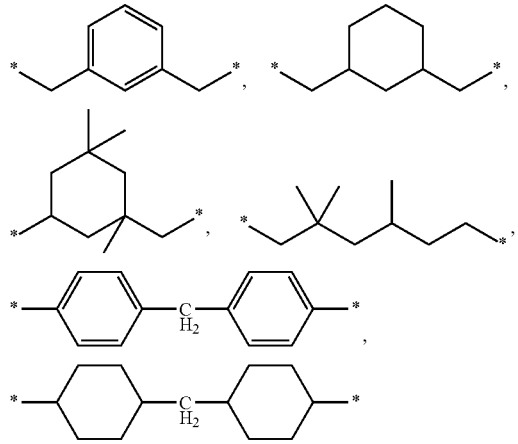

wherein * denotes a bond.

The radical can be derived from readily available diamines, for example, so called Jeffamines. Examples for diamines are Ethylenediamine, propylenediamine, 2-methyl-1,5-pentam-ethylenediamine, isophoronediamine or 1,2-diaminocyclo-hexane.

In analogy the radical Z can also be derived from the same available diamines or from the corresponding diols.

Typical Jeffamines are, for example D-2000

wherein x is 33.1 or ED-2003

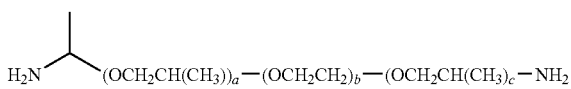

wherein a+c is 5 and b is 39.5.

For example in the compound of formula (I) Q is

$Y_{10}$ is $NR_{101}$
$X_{10}$ is O=C, S=C, $R_{101}$N;
$Z_{10}$ is O=C, S=C, $R_{101}$N, O, S(O)$_n$ where n is 0;
or $Y_{10}$ is O
$X_{10}$ is O=C, S=C;
$Z_{10}$ is $R_{101}$N;
or $Y_{10}$ is S
$X_{10}$ is O=C, S=C;
$Z_{10}$ is $R_{101}$N;
or Q is

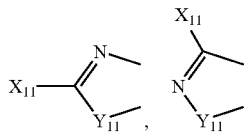

$X_{11}$ is $R_{101}$, $N(R_{101})_2$, $OR_{101}$, $S(O)_nR_{101}$ where n is 0;
$Y_{11}$ is C=O, $NR_{101}$, O, or $S(O)_n$ where n is 0;
or Q is

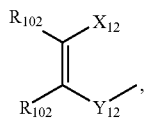

$X_{12}$ is C=O;
$Y_{12}$ is $NR_{101}$, O or S;
or Q is

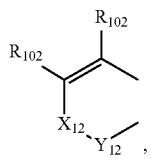

$X_{12}$ is C=O;
$Y_{12}$ is $NR_{101}$, O or S;
or Q is

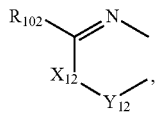

$X_{12}$ is C=O;
$Y_{12}$ is $NR_{101}$ or O;
or Q is

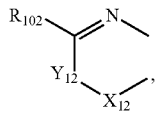

$X_{12}$ is C=O;
$Y_{12}$ is $NR_{101}$ or O;
or Q is

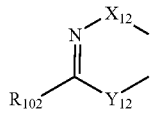

$X_{12}$ is C=O;
$Y_{12}$ is $NR_{101}$ or O;
or Q is

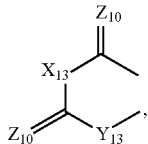

$X_{13}$ is $NR_{101}$, O or S;
$Y_{13}$ is $NR_{101}$;
$Z_{10}$ is O;
or Q is

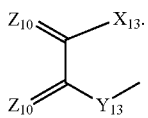

$X_{13}$ is $NR_{101}$;
$Y_{13}$ is $NR_{101}$;
$Z_{10}$ is O;
$R_{101}$ is hydrogen, straight or branched chain $C_1$-$C_{24}$alkyl, straight or branched chain $C_2$-$C_{18}$alkenyl, $C_2$-$C_6$alkinyl, $C_5$-$C_{12}$cycloalkyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more -halogen, —OH, —$OR_{22}$, —$NH_2$, —$NHR_{22}$, —$N(R_{22})_2$, —$NHCOR_{23}$, —$NR_{22}COR_{23}$, —$OCOR_{24}$, —$COR_{25}$, —$SO_2R_{26}$, —$SO_3^-M^+$, —PO$(R_{27})_n(R_{28})_{2-n}$, —Si$(R_{29})_n(R_{30})_{3-n}$, —Si$(R_{22})_3$, —$N^+(R_{22})_3A^-$, —$S^+(R_{22})_2A^-$ or combinations thereof; said straight or branched chain unsubstituted or substituted $C_1$-$C_{24}$ alkyl, straight or branched chain unsubstituted or substituted $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;
said phenyl, naphthyl or $C_7$-$C_{15}$phenylalkyl can also be substituted by one or more -halogen, —CN, —$CF_3$, —$NO_2$, —$NHR_{22}$, —$N(R_{22})_2$, —$SO_2R_{26}$, —PO$(R_{27})_n(R_{28})_{2-n}$, —OH, —$OR_{22}$, —$COR_{25}$, —$R_{25}$; wherein
n is 0, 1 or 2;
$R_{22}$ is straight or branched chain $C_1$-$C_{18}$ alkyl, straight or branched chain $C_2$-$C_{18}$ alkenyl, $C_5$-$C_{10}$ cycloalkyl, phenyl or naphthyl, $C_7$-$C_{15}$ phenylalkyl, or two $R_{22}$ when attached to an N or Si atom can form together with the atom to which they are bonded a pyrrolidine, piperidine or morpholine ring;
$R_{23}$ is hydrogen, $OR_{22}$, $NHR_{22}$, $N(R_{22})_2$ or has the same meaning as $R_{22}$,
$R_{24}$ is $OR_{22}$, $NHR_{22}$, $N(R_{22})_2$ or has the same meaning as $R_{22}$,
$R_{25}$ is hydrogen, OH, $OR_{22}$, $NHR_{22}$ or $N(R_{22})_2$, or has the same meaning as $R_{22}$,
$R_{26}$ is OH, $OR_{22}$, $NHR_{22}$ or $N(R_{22})_2$,
$R_{27}$ is $NH_2$, $NHR_{22}$ or $N(R_{22})_2$,
$R_{28}$ is OH or $OR_{22}$,
$R_{29}$ is Cl or $OR_{22}$,
$R_{30}$ is straight or branched chain $C_1$-$C_{18}$ alkyl; and $R_{102}$ is hydrogen, —CN, —$COR_{24}$ straight or branched chain $C_1$-$C_{24}$alkyl, straight or branched chain $C_2$-$C_{18}$alkenyl, $C_2$-$C_6$alkinyl, $C_5$-$C_{12}$cycloalkyl, phenyl, naphthyl or $C_7$-$C_{15}$-phenylalkyl.

Preferred is a compound of formula (I) wherein Q is

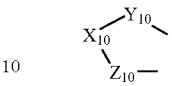

$Y_{10}$ is $NR_{101}$
$X_{10}$ is O=C, S=C
$Z_{10}$ is O=C, $R_{101}$N, O, S(O)$_n$ where n is 0;
or
$Y_{10}$ is $NR_{101}$
$X_{10}$ is $NR_{101}$
$Z_{10}$ is O=C;
or Q is

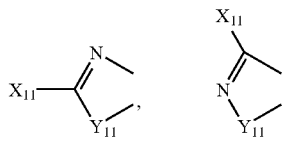

$X_{11}$ is $R_{101}$;
$Y_{11}$ is C=O, $NR_{101}$, O, or S(O)$_n$ where n is 0;
or Q is

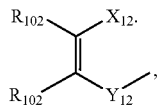

$X_{12}$ is C=O;
$Y_{12}$ is $NR_{101}$ or O;
or Q is

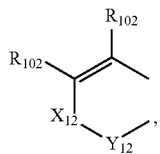

$X_{12}$ is C=O;
$Y_{12}$ is $NR_{101}$ or O;
or Q is

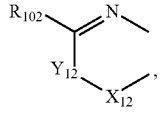

$X_{12}$ is C=O;
$Y_{12}$ is $NR_{101}$ or O;
or Q is

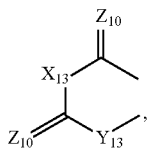

$X_{13}$ is $NR_{101}$;
$Y_{13}$ is $NR_{101}$;
$Z_{10}$ is O;
or Q is

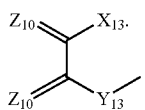

$X_{13}$ is $NR_{101}$;
$Y_{13}$ is $NR_{101}$;
$Z_{10}$ is O;

$R_{101}$ is hydrogen, straight or branched chain $C_1$-$C_{24}$alkyl, straight or branched chain $C_2$-$C_{18}$alkenyl, $C_2$-$C_6$alkinyl, $C_5$-$C_{12}$cycloalkyl, phenyl, naphthyl or $C_7$-$C_{15}$phenylalkyl; said straight or branched chain said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more —OH; or can also be interrupted by one or more —O—, —S—, —NH— or —$NR_{22}$— groups or combinations thereof;

$R_{22}$ is straight or branched chain $C_1$-$C_{18}$ alkyl, straight or branched chain $C_2$-$C_{18}$ alkenyl, $C_5$-$C_{10}$ cycloalkyl, phenyl or naphthyl or $C_7$-$C_{15}$ phenylalkyl;

$R_{102}$ is hydrogen, —CN, —$COR_{24}$ straight or branched chain $C_1$-$C_{24}$alkyl, straight or branched chain $C_2$-$C_{18}$alkenyl, $C_2$-$C_6$alkinyl, $C_5$-$C_{12}$cycloalkyl, phenyl, naphthyl or $C_7$-$C_{15}$phenylalkyl; and $R_{24}$ is $OR_{22}$, $NHR_{22}$, $N(R_{22})_2$ or has the same meaning as $R_{22}$.

Particularly preferred is a compound of formula (I) wherein
$R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or
$R_1$ is a group

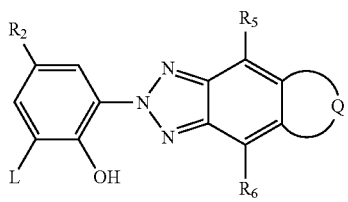

wherein L is alkylene of 1 to 12 carbon atoms, alkylidene of 2 to 12 carbon atoms, benzylidene, p-xylylene or cycloalkylene of 5 to 7 carbon atoms;

$R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $R_2$ is —$(CH_2)_m$—CO—$X_1$—$(Z)_p$—Y—$R_{15}$ wherein
$X_1$ is —O—,
Y is —O— or a direct bond,
Z is $C_2$-$C_{12}$-alkylene, $C_4$-$C_{12}$alkylene interrupted by one to three nitrogen atoms, oxygen atoms or a mixture thereof, or when Y is a direct bond, Z can additionally also be a direct bond;
m is 2,
p is 1,
$R_{15}$ is hydrogen, $C_1$-$C_{12}$alkyl or a group

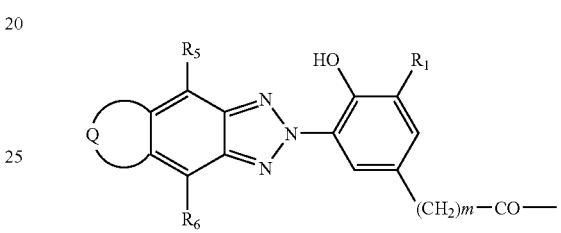

$R_5$ and $R_6$ are independently hydrogen or $C_1$-$C_4$alkyl.

For instance, in the compound of formula (I)
$R_1$ is hydrogen, straight or branched chain alkyl of 1 to 12 carbon atoms or phenylalkyl of 7 to 15 carbon atoms;
$R_2$ is straight or branched chain alkyl of 1 to 12 carbon atoms or phenylalkyl of 7 to 15 carbon atoms, phenyl, or said phenyl or said phenylalkyl substituted on the phenyl ring by 1 to 3 alkyl of 1 to 4 carbon atoms;
$R_5$ and $R_6$ are hydrogen or $C_1$-$C_4$alkyl.

More preferred is a compound of formula (I) which is a compound according to formulae (a) to (i)

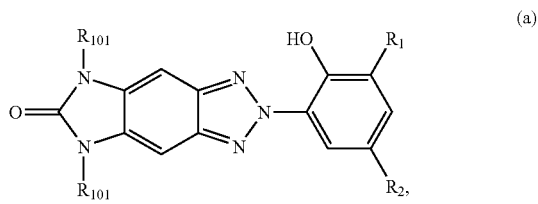

(a)

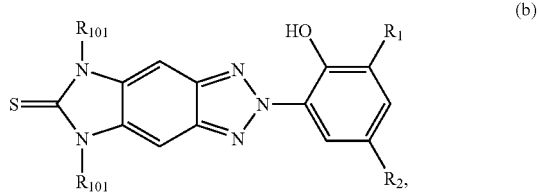

(b)

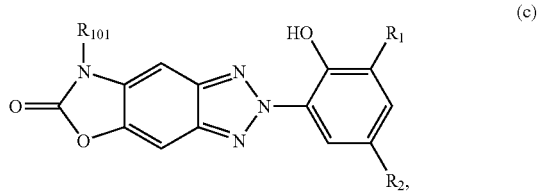

(c)

-continued

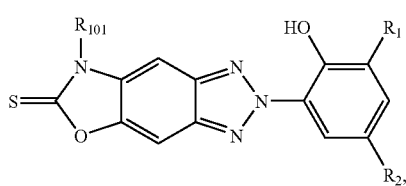
(d)

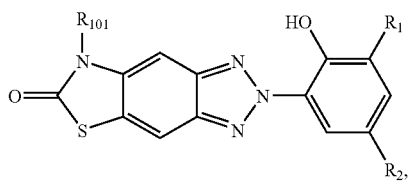
(e)

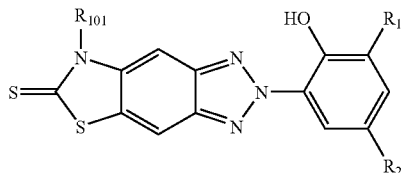
(f)

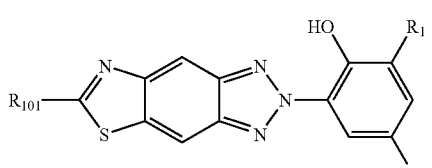
(g)

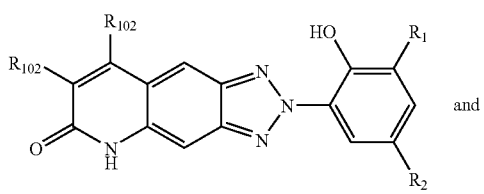
(h)

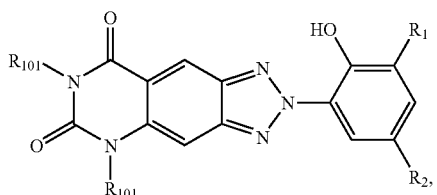
and

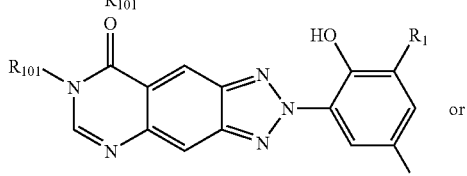
or

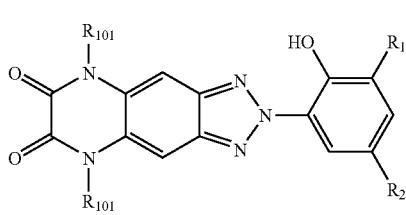

wherein $R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms;

$R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $R_2$ is $-(CH_2)_m-CO-X_1-(Z)_p-Y-R_{15}$ wherein $X_1$ is $-O-$, Y is $-O-$ or a direct bond, Z is $C_2-C_{12}$-alkylene, $C_4-C_{12}$alkylene interrupted by one to three nitrogen atoms, oxygen atoms or a mixture thereof, or when Y is a direct bond, Z can additionally also be a direct bond;

m is 2, p is 1, $R_{15}$ is hydrogen, $C_1-C_{12}$alkyl;

$R_5$ and $R_6$ are hydrogen;

$R_{101}$ is hydrogen, straight or branched chain $C_1-C_{24}$alkyl, straight or branched chain $C_2-C_{18}$alkenyl, $C_2-C_6$alkinyl, $C_5-C_{12}$cycloalkyl, phenyl, naphthyl or $C_7-C_{15}$phenylalkyl; said straight or branched chain $C_1-C_{24}$ alkyl, straight or branched chain $C_2-C_{24}$ alkenyl, $C_5-C_{12}$ cycloalkyl, $C_2-C_6$ alkinyl can be substituted by one or more $-OH$; or said straight or branched chain unsubstituted or substituted $C_1-C_{24}$ alkyl, straight or branched chain $C_2-C_{24}$ alkenyl, $C_5-C_{12}$ cycloalkyl or $C_2-C_6$ alkinyl can also be interrupted by one or more $-O-$, $-S-$, $-NH-$ or $-NR_{22}-$ groups or combinations thereof;

$R_{22}$ is straight or branched chain $C_1-C_{18}$ alkyl, straight or branched chain $C_2-C_{18}$ alkenyl, $C_5-C_{10}$ cycloalkyl, phenyl or naphthyl or $C_7-C_{15}$ phenylalkyl;

$R_{102}$ is hydrogen, $-CN$, $-COR_{24}$ straight or branched chain $C_1-C_{24}$alkyl, straight or branched chain $C_2-C_{18}$alkenyl, $C_2-C_6$alkinyl, $C_5-C_{12}$cycloalkyl, phenyl, naphthyl or $C_7-C_{15}$phenylalkyl; and $R_{24}$ is $OR_{22}$, $NHR_{22}$, $N(R_{22})_2$ or has the same meaning as $R_{22}$.

Another aspect of the invention is a process for the preparation of a compound of formula (I)

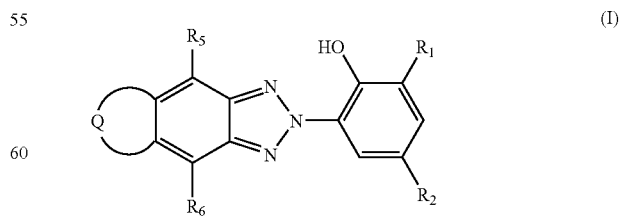
(I)

wherein the substituents $R_1$ to $R_6$ and Q are as defined above, which process comprises reacting a compound of formulae (III)

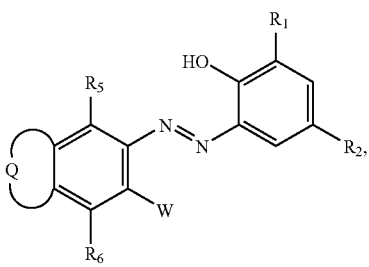

(III)

wherein W is halogen or nitro
with an azide compound of formula (X)

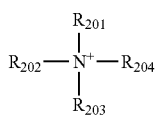

(X)

wherein
M is an n-valent metal cation, $$R_{202}-\underset{\underset{R_{203}}{|}}{\overset{\overset{R_{201}}{|}}{N^+}}-R_{204}$$

or $P^+(R_{205})_4$,
$R_{201}$, $R_{202}$, $R_{203}$ and $R_{204}$ are each independently of the others hydrogen or $C_1$-$C_{18}$alkyl,
$R_{205}$ is $C_1$-$C_{18}$alkyl, and
r is 1, 2 or 3.

Preferred reaction conditions of the process according to the invention are as follows:

The reaction can be carried out in the melt or in a solvent. Of special interest is a process for the preparation of compounds of formula I or II wherein the reaction is carried out in a solvent.

Suitable solvents are, for example, dipolar aprotic solvents, protic solvents, esters of aliphatic or aromatic carboxylic acids, ethers, halogenated hydrocarbons, aromatic solvents, amines and alkoxybenzenes.

Examples of dipolar aprotic solvents are dialkyl sulfoxides, for example dimethyl sulfoxide; carboxamides, for example formamide, dimethylformamide or N,N-dimethylacetamide; lactams, for example N-methylpyrrolidone; phosphoric amides, for example hexamethylphosphoric triamide; alkylated ureas, for example N,N'-dimethylethyleneurea, N,N'-dimethylpropyleneurea or N,N,N',N'-tetramethylurea; and nitriles, for example acetonitrile or benzonitrile.

Examples of protic solvents are polyalkylene glycols, for example polyethylene glycol; polyalkylene glycol monoethers, for example diethylene glycol monomethyl ether, and water, the latter on its own or in a single-phase or two-phase mixture with one or more of the solvents mentioned, it being possible also for phase transfer catalysts to be added, for example tetraalkylammonium salts, tetraalkylphosphonium salts or crown ethers. The same phase transfer catalysts can also be of use in solid/liquid form in the two-phase system.

Preferred esters of aliphatic or aromatic carboxylic acids are, for example, butyl acetate, cyclohexyl acetate and methyl benzoate.

Preferred ethers are, for example, dialkyl ethers, especially dibutyl ether, tetrahydrofuran, dioxane and (poly-)alkylene glycol dialkyl ethers.

Halogenated hydrocarbons are, for example, methylene chloride and chloroform.

Aromatic solvents are, for example, toluene, chlorobenzene and nitrobenzene.

Suitable amine solvents are, for example, triethylamine, tributylamine and benzyl-dimethylamine.

Preferred alkoxybenzenes are, for example, anisole and phenetole.

The process for the preparation of compounds of formula I can also be carried out in ionic or supercritical fluids, for example fluid carbon dioxide.

Of special interest is a process for the preparation of compounds of formula I wherein the reaction is carried out in a dipolar aprotic solvent.

The reaction temperatures can be varied within wide limits but are so selected that satisfactory conversion occurs, such temperatures preferably being from 10° to 200° C., especially from 20° to 150° C.

An analogous process for other benzotriazole compounds has already been disclosed in WO 02/24668.

Preference is given to a process for the preparation of compounds of formula I wherein the molar ratio of the amount of a compound of formula III to the amount of the azide compound of formula X is from 1:1 to 1:3, especially from 1:1 to 1:2, e.g. from 1:1 to 1:1.3. When functional side groups that are also able to react with azide are present, the excess of the azide compound of formula X is increased accordingly.

In a specific embodiment the reaction is carried out in the presence of a catalyst.

Such catalysts include, for example, copper(I) or copper (II) salts or other transition metal salts, based, for example, on iron, cobalt, nickel, palladium, platinum, gold or zinc. Instead of transition metal salts, the anions of which can be varied within wide limits, it is also possible to use metal complexes and metal complex salts of the same metals as catalysts. Preference is given to the use of copper(I) and copper(II) chlorides, bromides and iodides, and special preference to the use of copper(I) bromide.

The catalyst is advantageously used in an amount of from 0.01 to 10% by weight, especially from 0.1 to 5% by weight, e.g. from 0.1 to 5% by weight, based on the weight of the compound of formula III, IV or V employed.

The reaction can also be carried out in the presence of an additional base or in the presence of an alkaline pH buffer system. Suitable pH buffer systems include, for example, alkali metal or alkaline earth metal hydroxides; alkali metal or alkaline earth metal alcoholates; alkali metal or alkaline earth metal carboxylates, for example acetates or carbonates; alkali metal or alkaline earth metal phosphates; tertiary amines, for example triethylamine or tributylamine; and unsubstituted or substituted pyridines.

Some of the starting compounds of formula III are known from the literature or can be prepared analogously to the procedures described in the examples.

It is, however, also possible to prepare the instant benzotriazoles by conventional methods for preparing such compounds.

Consequently another aspect of the invention is an alternative process for the preparation of a compound of formula (I)

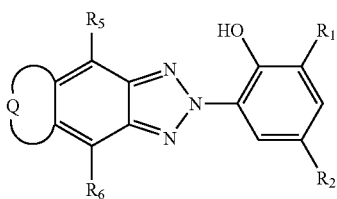

(I)

wherein the substituents $R_1$ to $R_6$ and Q are as above, which process comprises reacting a compound of formula (III)

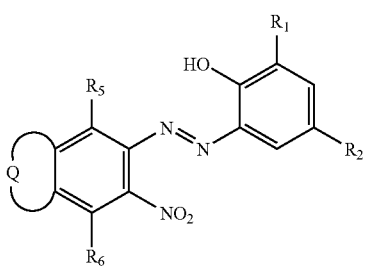

(III)

under reductive conditions to a compound of formula (I).

The usual procedure involves the diazotization of a substituted o-nitroaniline followed by coupling the resultant diazonium salt with a substituted phenol and reduction of the azobenzene intermediate to the corresponding desired benzotriazole. Such processes are described, for example, in U.S. Pat. No. 5,276,161 and U.S. Pat. No. 5,977,219. The starting materials for these benzotriazoles are partly items of commerce or can be prepared by normal methods of organic synthesis.

Further methods for the preparation of benzotriazoles are for example given in Science of Synthesis 13.13, 575-576.

The reduction process can not only be carried out by hydration but also by other methods, such as for example described in EP 0 751 134. When a H-transfer is made, reagents, such as formic acid or its salts, phosphinic acid or its salts or an alkali metal or ammonium salt of hypophosphoric acid together with a catalyst may be useful. The catalyst is, for example, a precious metal.

A further aspect of the invention is a compound of formula (IV)

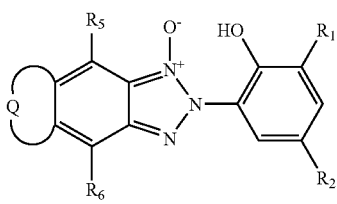

(IV)

wherein the substituents $R_1$ to $R_6$ and Q are as defined above.

These compounds are, when isolated, intermediates of the compounds according to formula (I).

The benzotriazoles of the present invention are generally useful as UV-absorbers in various substrates. Consequently a further aspect of the invention is a composition stabilized against light-induced degradation which comprises, (a) an organic material subject to light-induced degradation, and
(b) a compound of formula I as described above.

In general the compound of formula I is present in an amount from 0.1% to 30%, preferably from 0.5% to 15% and more preferably from 1% to 10% by weight, based on the weight of the organic material.

In one aspect the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example paper or plastic film, which has been coated with one or more layers. Depending on the type of the material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 (incorporated herein by reference).

The recording material can also be transparent, as, for example, in the case of projection films.

The compounds of the formula I can be incorporated into the carder material as early as the production of the latter, in the production of paper, for example, by being added to the paper pulp. A second method of application is to spray the carder material with an aqueous solution of compounds of the formula I or to add the compounds to the coating composition.

Coating compositions intended for transparent recording materials suitable for projection cannot contain any particles which scatter light, such as pigments and fillers.

The dye-binding coating composition can contain a number of other additives, for example antioxidants, light stabilizers (including also UV absorbers which do not belong to the UV absorbers according to the invention), viscosity improvers, fluorescent brighteners, biocides and/or antistatic agents.

The coating composition is usually prepared as follows: the water-soluble components, for example the binder, are dissolved in water and stirred together. The solid components, for example fillers and other additives already described, are dispersed in this aqueous medium. Dispersion is advantageously carded out by means of devices, for example ultrasonic samples, turbine stirrers, homogenizers, colloid mills, bead mills, sand mills, high-speed stirrers and the like. The compounds of the formula I can be incorporated easily into the coating composition.

The recording material according to this invention preferably contains 1 to 5000 mg/m$^2$, in particular 50-1200 mg/m$^2$, of a compound of the formula I.

As already mentioned, the recording materials according to the invention embrace a wide field. The compounds of the formula I can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,5365,463; 4,551,407; 4,562,137 and 4,608,330, also in EP-A 139,479; EP-A 162,664; EP-A 164,931; EP-A 237,024; EP-A 237,025 or EP-A 260,129. In all these systems the compounds can be put into the dye-receiving layer. The compounds can, however, also be put into the donor layer in order to protect the color formers from light.

Photographic materials which can be stabilized are photographic dyes and layers containing such dyes or precursors thereof, for example photographic paper and films. Suitable materials are, for example, described in U.S. Pat. No. 5,364,749 (incorporated therein by reference). The compounds of the formula I act here as a UV filter against electrostatic flashes. In color photographic materials couplers and dyes are also protected against photochemical decomposition.

The instant compounds can be used for all types of color photographic materials. For example, they can be employed for color paper, color reversal paper, direct-positive color material, color negative film, color positive film, color reversal film, etc. They are preferably used, inter alia, for photographic color material which contains a reversal substrate or forms positives.

Color-photographic recording materials usually contain, on a support, a blue-sensitive and/or a green-sensitive and/or a red-sensitive silver-halide emulsion layer and, if desired, a protection layer, the compounds being, preferably, either in the green-sensitive or the red-sensitive layer or in a layer between the green-sensitive and the red-sensitive layer or in a layer on top of the silver-halide emulsion layers.

The compounds of the formula I can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, they can be employed in recording materials for dye diffusion transfer printing, thermal wax transfer printing and not matrix printing and for use with electrostatic, electrographic, electrophoretic, magnetographic and laser-electrophotographic printers and pen-plotters. Of the above, recording materials for dye diffusion transfer printing are preferred as, for example described in EP-A-507,734.

They can also be employed in inks, preferably for ink jet printing, as, for example, further described in U.S. Pat. No. 5,098,477 (incorporated herein by reference).

In another specific embodiment of the invention the organic material is a natural, semisynthetic or synthetic polymer.

Examples of such polymers are given below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).
b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethyleneacrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4-trimethylhexamethylene terephthalamide or polym-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

For example the polymer is a thermoplastic polymer.

In another embodiment the organic material is a coating, in particular an automotive coating.

Resins used in coatings are typically crosslinked polymers, for example, derived from aldehydes on the one hand and phenols, ureas and melamines on the other hand, such as phenol/formaldehyde resins, urea/formaldehyde resins and melamine/formaldehyde resins.

Also useful are unsaturated polyester resins derived from copolyesters of saturated and unsaturated dicarboxylic acids with polyhydric alcohols and vinyl compounds as crosslinking agents, and also halogen-containing modifications thereof of low flammability.

Preferably used are crosslinkable acrylic resins derived from substituted acrylates, for example epoxy acrylates, urethane acrylates or polyester acrylates.

Also possible are alkyd resins, polyester resins and acrylate resins crosslinked with melamine resins, urea resins, isocyanates, isocyanurates, polyisocyanates or epoxy resins.

Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

The coating material may also be a radiation curable composition containing ethylenically unsaturated monomers or oligomers and a polyunsaturated aliphatic oligomer.

The alkyd resin lacquers which can be stabilized against the action of light in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99-123). Other crosslinking agents include glycouril resins, blocked isocyanates or epoxy resins.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When water-soluble, water miscible or water dispersible coatings are desired ammonium salts of acid groups present in the resin are formed. Powder coating composition can be prepared by reacting glycidyl methacrylate with selected alcohol components.

In a specific embodiment the above mentioned coating is applied over a substrate, which is sensitive to electromagnetic radiation of wavelengths greater than 380 nm.

A typical sensitive substrate is, for example, a cathodically deposited coating adhering to a metal substrate. Such coatings are typically used in the automotive industry.

Under sensitive to electromagnetic radiation of wavelengths greater than 380 nm there is understood UV or visible light, for example, in the wavelength range up to 440 nm, preferably up to 420 nm and in particular up to 410 nm.

For example the composition of the automotive coating comprises a) a primer coat which is electrodeposited onto a metal substrate;

b) at least one pigmented base coat which is in direct contact with the primer coat, containing a compound of formula (I) according to claim 1;

c) a clear coat which is in direct contact with the pigmented base coat, containing a UV-absorber selected from the group consisting of the s-triazines, the oxanilides, the hydroxybenzophenones, benzoates, the α-cyanoacrylates and the benzotriazoles different from those of formulae (I) and d) optionally the clear coat contains also a compound of formula (I).

In a specific embodiment the above composition contains also in the primer coat a compound of formula (I).

In the various organic materials, in which the compounds of formula (I) are useful as stabilizers against the deleterious influence of UV and/or visible light further stabilizers and additives may be also present.

Examples are subsequently given.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-d i-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-(3-(3-tert-butyl-4-hydroxy-5-methylphenyl)propionyloxy)-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as nbutylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tertoctylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-penta methyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydrooxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis-[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydrooxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-[2-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos®168, Ciba Specialty Chemicals Inc.), tris(nonylphenyl)phosphite,

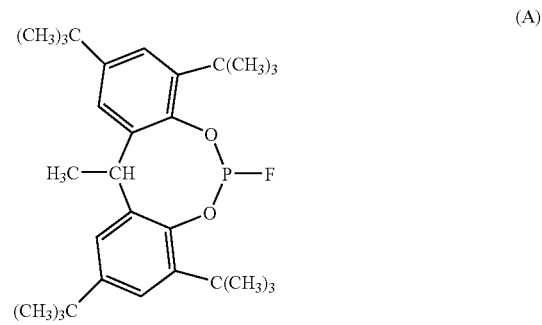

(A)

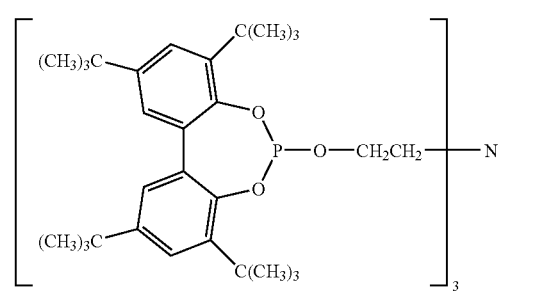

(B)

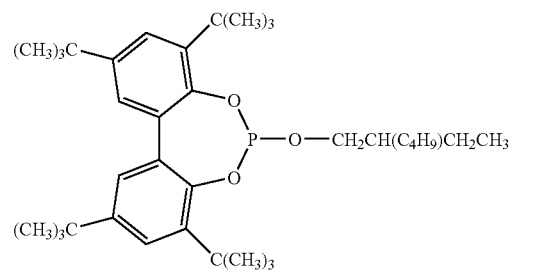

(C)

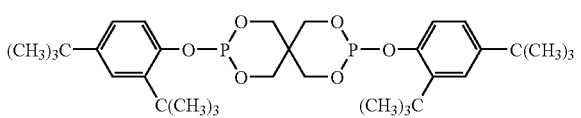

(D)

(E)

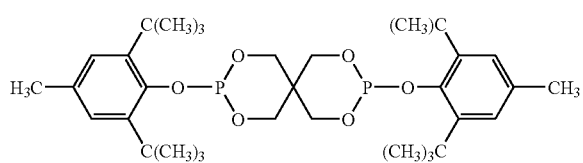

(F)

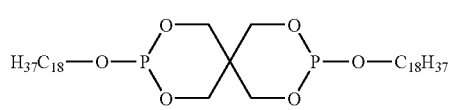

(G)

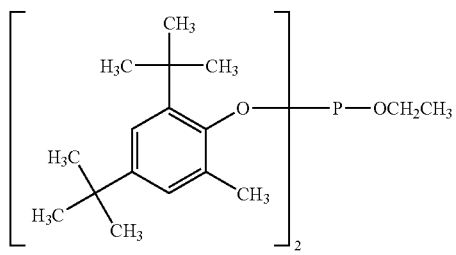

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-octadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of 8-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyl oxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-on e, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctylbenzofuran-2-one.

Preferably the compositions above contain additionally a sterically hindered amine stabilizer and/or a UV absorber selected from the group consisting of the s-triazines, the oxanilides, the hydroxybenzophenones, benzoates, the α-cyanoacrylates and the benzotriazoles different from those of formulae (I) as described above.

When additional UV-absorbers are added they are preferably added in an amount from 0.1% to 30%, more preferably from 0.5% to 15% and most preferably from 1% to 10% by weight, based on the weight of the organic material.

When a hindered amine light stabilizer is additionally added it is preferably added in an amount from 0.1% to 10%, more preferably from 0.5% to 5% and most preferably from 1% to 3% by weight, based on the weight of the organic material.

The total amount of UV-absorber of formula I and other UV-absorbers and/or hindered amine stabilizer is for example from 0.5% to 15% by weight, based on the weight of the organic material.

Examples for the hindered amine light stabilizers and UV-absorbers of the different classes are given above.

Particularly preferred UV-absorbers are the following s-triazines and benzotriazoles:

33
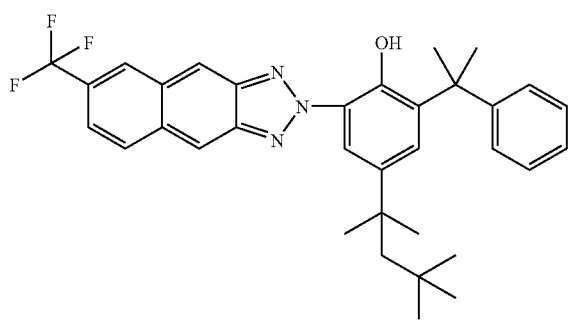
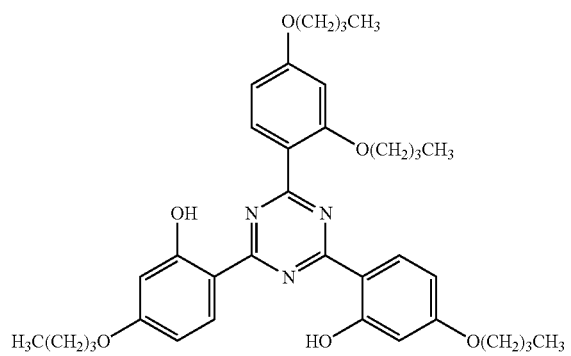
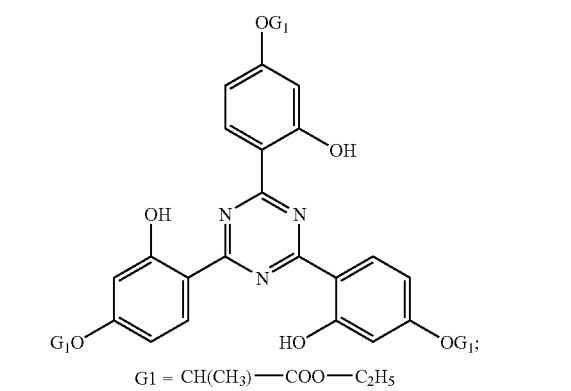
G1 = CH(CH₃)—COO—C₂H₅
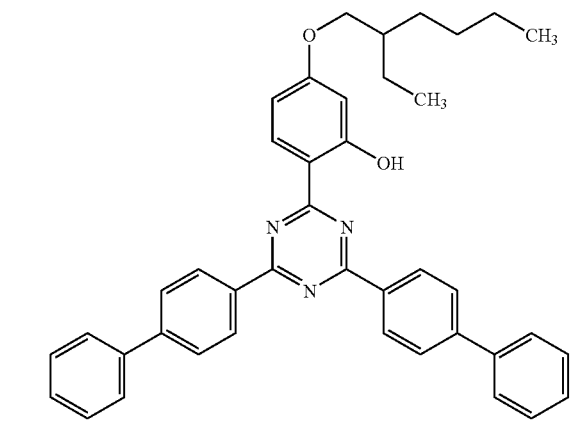
34
-continued
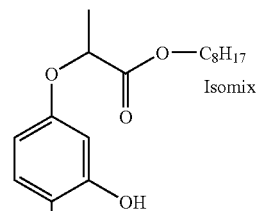
Isomix
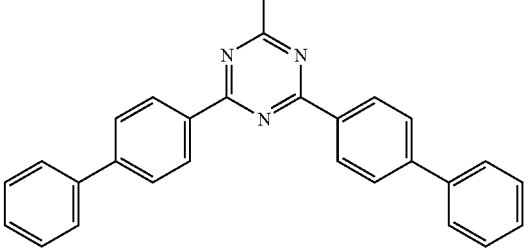
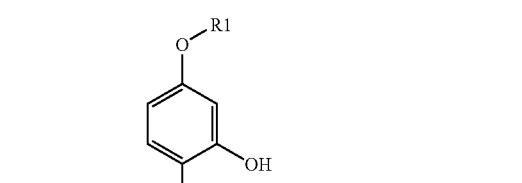
= a mixture of
a) R1 = R2 = CH(CH₃)—COO—C₈H₁₇, R3 = R4 = H;
b) R1 = R2 = R3 = CH(CH₃)—COO—C₈H₁₇, R = H;
c) R1 = R2 = R3 = R4 = CH(CH₃)—COO—C₈H₁₇
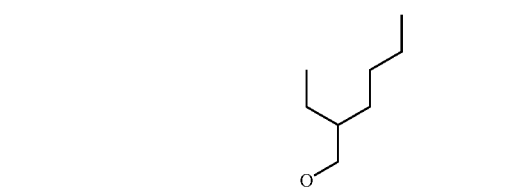
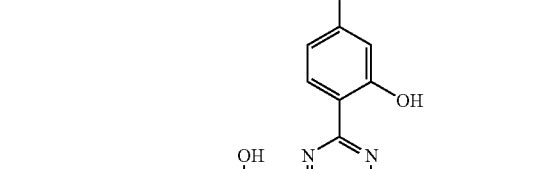
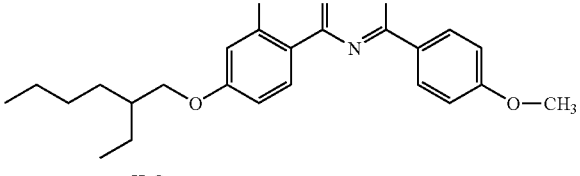
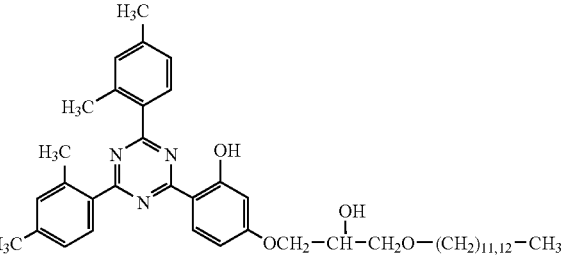

-continued

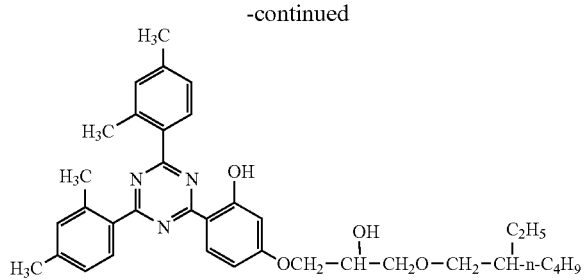

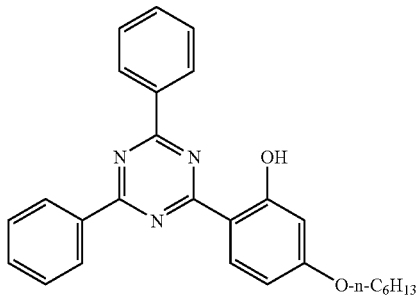

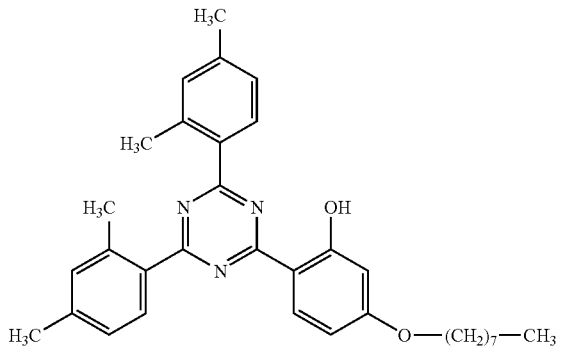

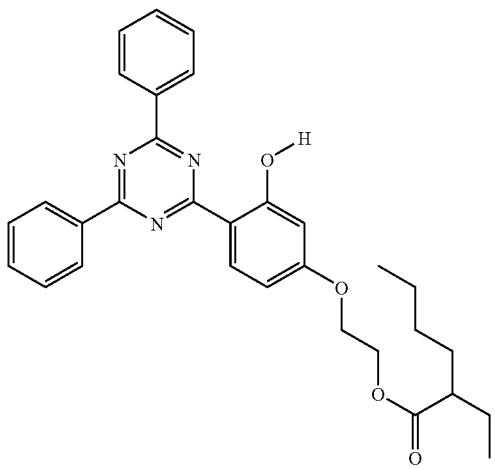

The hydroxyphenyl triazine UV-absorbers are known and are partially items of commerce.

The most suitable benzotriazole UV-absorbers are commercially available under the Trade Names TINUVIN 384®, TINUVIN 928®, TINUVIN 900®, TINUVIN 328® and TINUVIN 1130®.

The sterically hindered amine compounds of component (c) are preferably selected from the group consisting of the following commercial products: DASTIB 845®, TINUVIN 770®, TINUVIN 765®, TINUVIN 144®, TINUVIN 123®, TINUVIN 111®, TINUVIN 783®, TINUVIN 791®, TINUVIN 123®, TINUVIN 292®, TINUVIN 152®, TINUVIN 144®, MARK LA 52®, MARK LA 57®, MARK LA 62®, MARK LA 67®, HOSTAVIN N 20®, HOSTAVIN N 24®, SANDUVOR 3050®, SANDUVOR 3058®, DIACETAM 5®, SUMISORB TM 61®, UVINUL 4049®, SANDUVOR PR 31®, GOODRITE UV 3034®, GOODRITE UV 3150®, GOODRITE UV 3159®, GOODRITE 3110×128®, UVINUL 4050H®, CHIMASSORB 944®, CHIMASSORB 2020®, CYASORB UV 3346®, CYASORB UV 3529®, DASTIB 1082®, CHIMASSORB 119®, UVASIL 299®, UVASIL 125®, UVASIL 2000®, UVINUL 5050H®, LICHTSCHUTZSTOFF UV 31®, LUCHEM HA B 18®, MARK LA 63®, MARK LA 68®, UVASORB HA 88®, TINUVIN 622®, HOSTAVIN N 30® and FERRO AM 806®.

Particularly preferred are TINUVIN 770®, TINUVIN 292®, TINUVIN 123®, TINUVIN 144® and TINUVIN 152®.

Yet another aspect of the invention is the use of a compound of formula I as ultraviolet (UV) and visible (VIS) light absorber in organic materials.

The definitions and preferences given for the compounds apply also for the other aspects of the invention.

The following examples illustrate the invention.

A) PREPARATION EXAMPLES

Example A1

Preparation of Compound 1b

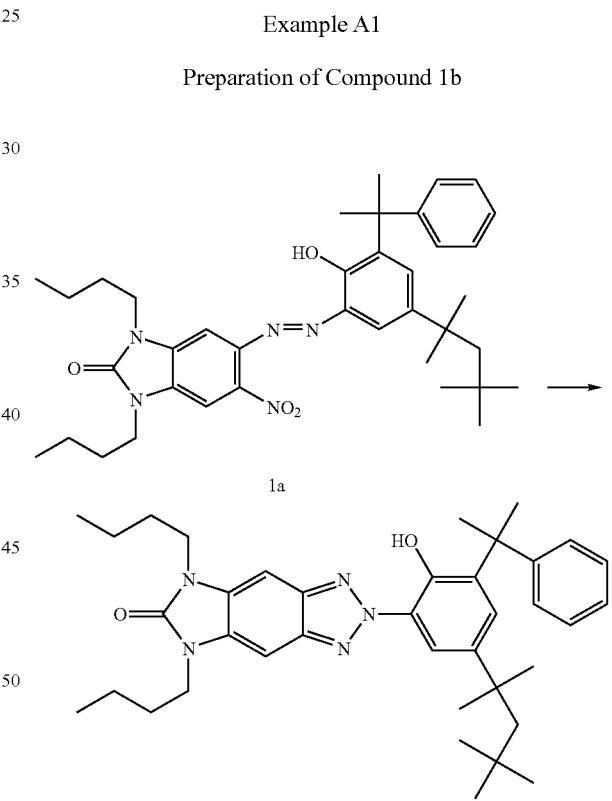

A stirred mixture of compound 1a (40.0 g, 62 mmol), sodium azide (99%; 6.1 g, 93 mmol) and 1-methyl-2-pyrrolidinone (150 ml) is heated to 160° C. The temperature is maintained and the progress of reaction is monitored by TLC (6.5 hours). The dark solution is cooled over night to room temperature followed by the addition of water (1000 ml) and ethyl acetate (1500 ml). The water phase is split off and washed with ethyl acetate (1×250 ml). The combined organic phases are washed with water (3×100 ml), dried (Na$_2$SO$_4$), filtered and the solvent evaporated. The residue is dissolved in hot methanol. After cooling the slightly pink precipitate is filtered off and recrystallized twice from acetone.

Yield 32.8 g (54 mmol, 57%)

Melting point: 148° C.

UV-vis (CHCl$_3$), $\lambda_{max}$/nm ($\epsilon$/dm$^3$ mol$^{-1}$ cm$^{-1}$): 364 (33520)

The above mentioned intermediate 1a is prepared as follows:

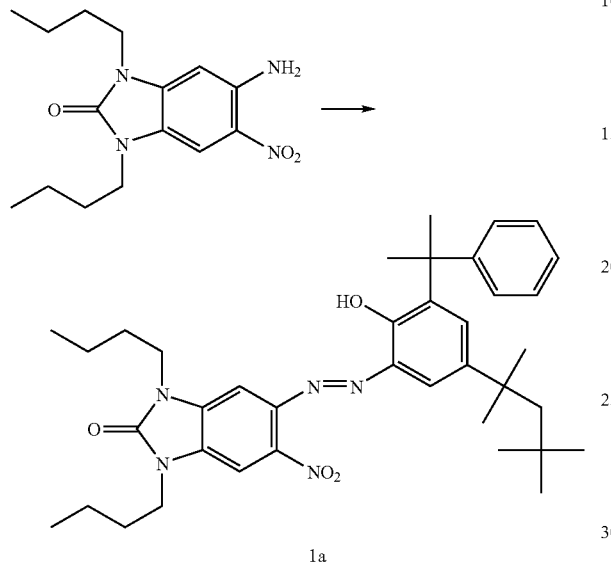

1a

Sodium nitrite (4 molar in water; 32.5 ml, 130 mmol) is slowly added between 0° C. and 5° C. to a stirred solution of 5-amino-1,3-dibutyl-6-nitro-benzimidazol-2-one (99.5%, 40.0 g, 130 mmol) in acetic acid (300 ml) containing hydrochloric acid (32% in water; 35 g). During the addition the temperature of the reaction mixture is kept between 0° C. and 5° C. by means of an ice bath. After the addition is complete (one hour), stirring is continued for 1.5 hours. The reaction mixture is then transferred into a dropping funnel and slowly added at −15° C. to a stirred solution of 2-cumyl-4-t-octylphenol (95%; 46.2 g, 135.0 mmol) in methanol (250 ml) containing sodium hydroxide microprills (5.5 g, 137.5 mmol). During the addition, the temperature of the reaction mixture is kept between −20° C. and −6° C. by means of an isopropanol-dry ice bath; the pH is measured by means of an electrode and held above 7 by concomitant addition of sodium hydroxide (30% in water; total of 350 ml). After the addition is complete (2 hours), the cooling bath is removed and the red suspension stirred overnight. After adding water (50 ml) and toluene (200 ml) the pH is brought to less than seven using hydrochloric acid (30% in water). The water phase is split off and washed with toluene (2×100 ml). The combined organic phases are washed with water, dried (Na$_2$SO$_4$), filtered and the solvent evaporated. Methanol (200 ml) is added and the resulting solution cooled by means of an ice bath. Compound 1a crystallizes as red solid, which is filtered off, washed with cold methanol and dried. Yield 63.9 g (99 mmol, 77%).

Melting point: 156° C.

Example A2

Preparation of Compound 1c

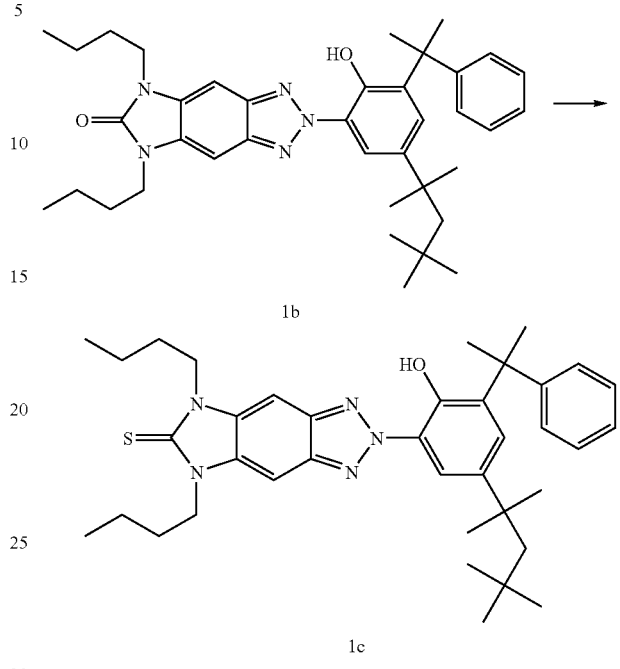

1b

1c

A stirred mixture of compound 1b (10.0 g, 16.4 mmol), Lawesson Reagent (98%; 16.2 g, 39.3 mmol) and xylene (500 ml) is heated to 130° C. The temperature is maintained and the progress of reaction is monitored by TLC (if necessary additional Lawesson Reagent is added). The reaction mixture is cooled to room temperature followed by the addition of water and ethyl acetate. The water phase is split off and washed with ethyl acetate. The combined organic phases are washed with water (3×), dried (Na$_2$SO$_4$), filtered and the solvent evaporated. The residue is chromatographed on a silica gel column (hexane/ethyl acetate 2:1) and the obtained product is recrystallized from isopropanol.

Yield 7.6 g (12.1 mmol, 74%)

Melting point: 137° C.

UV-vis (CHCl$_3$), $\lambda_{max}$/nm ($\epsilon$/dm$^3$ mol$^{-1}$ cm$^{-1}$): 388 (56795)

Example 3

Preparation of Compound 2b

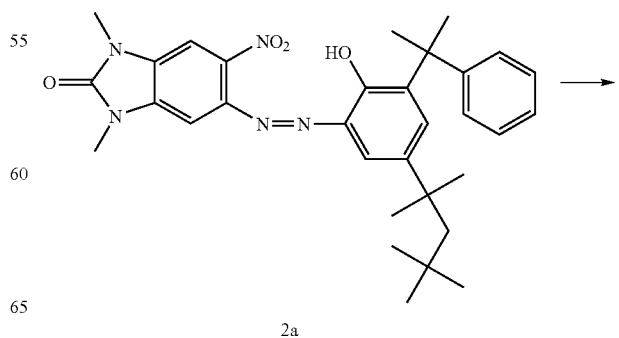

2a

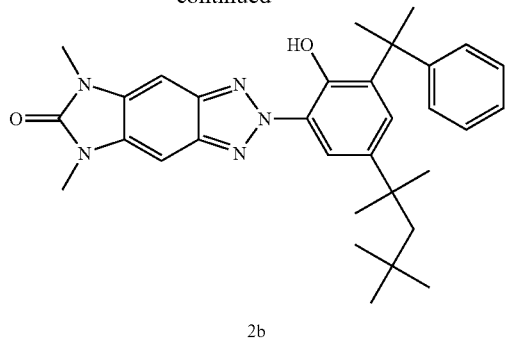

2b

A stirred mixture of compound 2a (8.9 g; 15.8 mmol), sodium azide (99%; 1.5 g; 23.1 mmol) and 1-methyl-2-pyrrolidinone (160 ml) is heated to 160° C. The temperature is maintained and the progress of reaction is monitored by TLC (16 hours). The dark solution is added in a stirred mixture of ice and water. The precipitate is filtered off and dried.

Yield 5.7 g (10.8 mmol, 69%)

Melting point: 187° C.

UV-vis (CHCl$_3$), $\lambda_{max}$/nm ($\epsilon$/dm$^3$ mol$^{-1}$ cm$^{-1}$): 362 (35288)

The above mentioned intermediate 2a is prepared as follows:

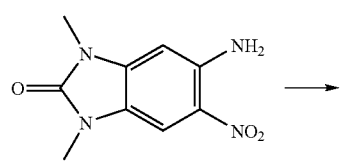

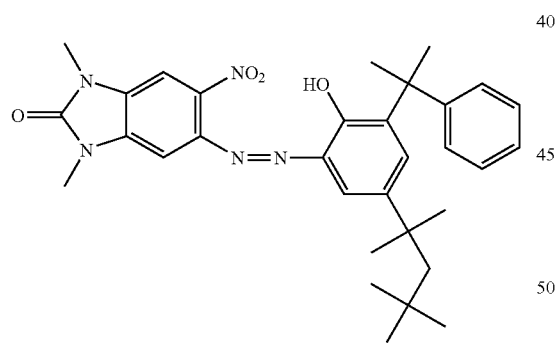

2a

Sodium nitrite (4 molar in water; 10 ml, 40 mmol) is slowly added between 0° C. and 5° C. to a stirred solution of 5-amino-1,3-dimethyl-6-nitro-benzimidazol-2-one (8 g, 36 mmol) in acetic acid (80 ml) containing hydrochloric acid (32% in water; 10 ml). During the addition the temperature of the reaction mixture is kept between 0° C. and 5° C. by means of an ice bath. After the addition is complete (15 minutes), stirring is continued for 1 hour. The reaction mixture is then transferred into a dropping funnel and slowly added at −30° C. to a stirred solution of 2-cumyl-4-t-octylphenol (95%; 11.6 g, 35.7 mmol) in methanol (50 ml) containing sodium hydroxide microprills (1.4 g, 36 mmol). During the addition, the temperature of the reaction mixture is kept between −20° C. and −5° C. by means of an isopropanol-dry ice bath; the pH is measured by means of an electrode and held above 7 by concomitant addition of sodium hydroxide (30% in water; total of 130 ml). After the addition is complete (1 hour), the cooling bath is removed and the red suspension stirred overnight. After adding brine (200 ml) and ethyl acetate (300 ml), the water phase is split off and washed with ethyl acetate (1×50 ml). The combined organic phases are washed with water, dried (Na$_2$SO$_4$), filtered and the solvent evaporated. Methanol (200 ml) is added and the resulting solution cooled by means of an ice bath. Compound 2a crystallizes as a brownish red solid, which is filtered off, Washed with cold methanol and dried. Yield 8.3 g (14.9 mmol, 41%).

Melting point: 269° C.

Example 4

Preparation of Compound 2c

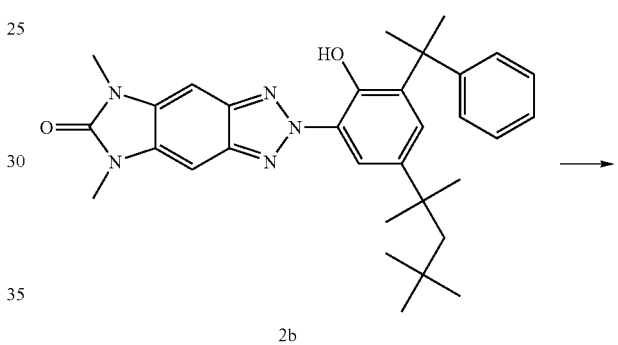

2b

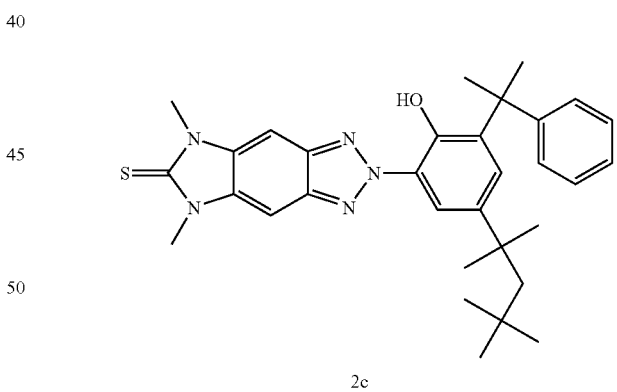

2c

A stirred mixture of compound 2b (2.7 g, 5.1 mmol), Lawesson Reagent (98%; 5.2 g, 12.5 mmol) and xylene (100 ml) is heated to 135° C. The temperature is maintained and the progress of reaction is monitored by TLC (if necessary additional Lawesson Reagent is added). The reaction mixture is concentrated to the half, cooled and filtered. The filtrate is concentrated to dryness and the residue is chromatographed on a silica gel column (hexane/ethyl acetate 1:1) and the obtained product is recrystallized from isopropanol.

Yield 2.4 g (4.2 mmol, 83%)

Melting point: 196° C.

UV-vis (CHCl₃), $\lambda_{max}$/nm ($\epsilon$/dm³ mol⁻¹ cm⁻¹): 386 (49570)

Example 5

Preparation of Compound 3b

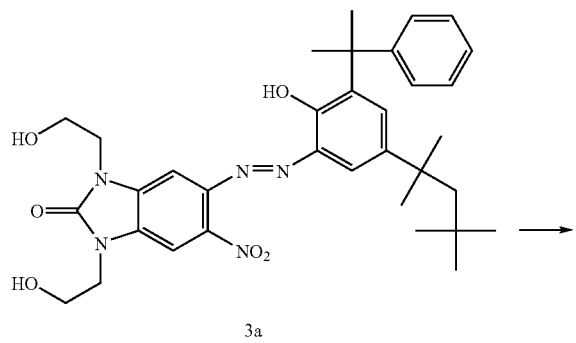

3a

3b

A stirred mixture of compound 3a (5.8 g; 9.4 mmol), sodium azide (99%; 0.91 g; 14.1 mmol) and 1-methyl-2-pyrrolidinone (150 ml) is heated to 160° C. The temperature is maintained and the progress of reaction is monitored by TLC (16 hours). The dark solution is added to a stirred mixture of ice and water. The precipitate is filtered off and chromatographed on a silica gel column (ethyl acetate/methanol 98:2)

Yield 2.3 g (39.3 mmol, 42%)

Melting point: 197° C.

UV-vis (CHCl₃), $\lambda_{max}$/nm ($\epsilon$/dm³ mol⁻¹ cm⁻¹): 363 (33922)

The above mentioned intermediate 3a is prepared as follows:

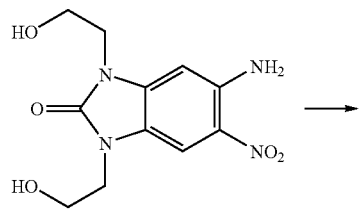

-continued

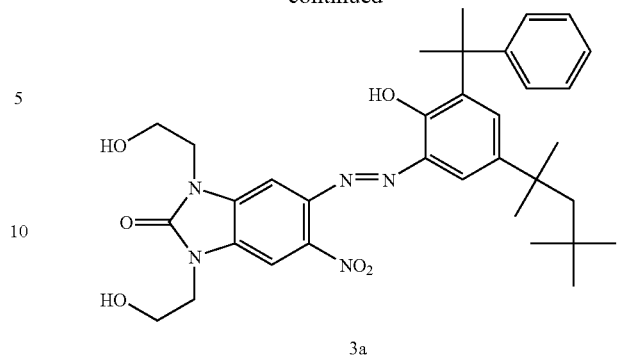

3a

Sodium nitrite (4 molar in water; 10 ml, 40 mmol) is slowly added between 0° C. and 5° C. to a stirred solution of 5-amino-1,3-dihydroxyethyl-6-nitro-benzimidazol-2-one (8.9 g, 3.5 mmol) in acetic acid (70 ml) containing hydrochloric acid (32% in water; 10 ml). During the addition the temperature of the reaction mixture is kept between 0° C. and 5° C. by means of an ice bath. After the addition is complete (15 minutes), stirring is continued for 1 hour. The reaction mixture is then transferred into a dropping funnel and slowly added at −20° C. to a stirred solution of 2-cumyl-4-t-octylphenol (95%; 10.7 g, 31.5 mmol) in methanol (50 ml) containing sodium hydroxide microprills (1.3 g, 31.5 mmol). During the addition, the temperature of the reaction mixture is kept between −20° C. and −5° C. by means of an isopropanol-dry ice bath; the pH is measured by means of an electrode and held above 7 by concomitant addition of sodium hydroxide (30% in water; total of 100 ml). After the addition is complete (1.5 hours), the cooling bath is removed and the red suspension stirred overnight. After adding brine (200 ml) the red residue is filtered off and chromatographed on a silica gel column (hexane/ethyl acetate 1:9) and the obtained product is recrystallized from methanol.

Yield 7.1 g (11.5 mmol, 37%)

Melting point: 211° C.

Example 6

Preparation of Compound 4b

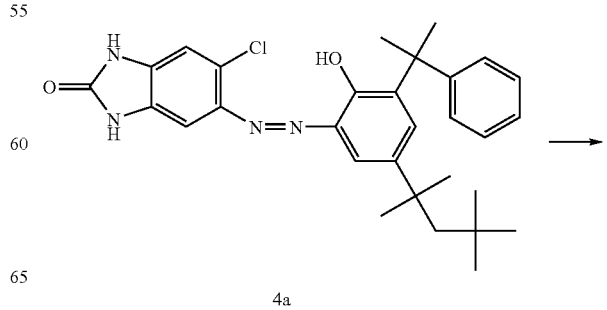

4a

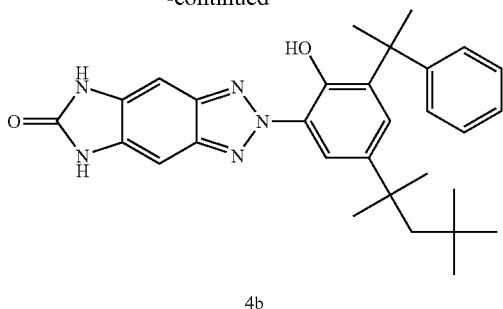

4b

A stirred mixture of compound 4a (10.4 g; 20 mmol), sodium azide (99%; 1.7 g; 26 mmol), copper(I) bromide (0.29 g; 2 mmol) and dimethyl formamide (40 ml) is heated to 130° C. The temperature is maintained and the progress of reaction is monitored by TLC (3.5 hours). The dark solution is added to a stirred mixture of ice and water. The precipitate is filtered off and chromatographed on a silica gel column (ethyl acetate/methanol 12:1)

Yield 2.5 g (5 mmol, 25%)

$^1$H-NMR (400 MHz, CDCl$_3$), δ (ppm): 11.23 (s broad, 1H), 9.01 (s broad, 2H), 8.26 (s, 1H), 7.61 (s, 1H), 7.33 (s, 2H), 7.31-7.29 (m, 4H), 7.20-7.17 (m, 1H), 1.82 (s, 6H), 1.79 (s, 2H), 1.28 (s, 6H), 0.80 (s, 9H).

UV-vis (dioxane), $\lambda_{max}$/nm (ε/dm$^3$ mol$^{-1}$ cm$^{-1}$): 359 (35801)

The above mentioned intermediate 4a is prepared as follows:

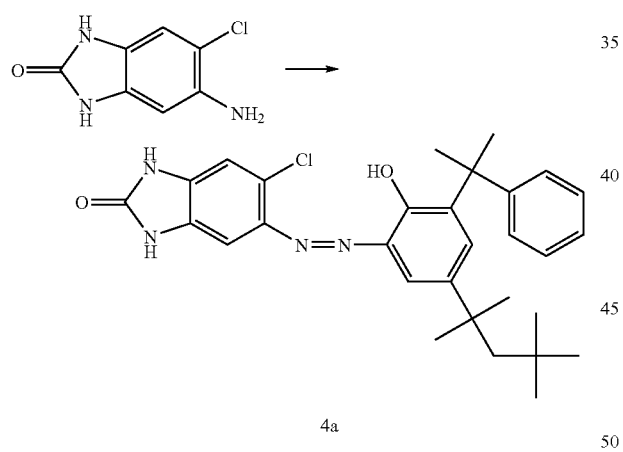

4a

Sodium nitrite (4 molar in water; 25 ml, 100 mmol) is slowly added between 0° C. and 5° C. to a stirred suspension of 5-amino-6-chloro-benzimidazol-2-one (18.36 g, 100 mmol) in acetic acid (250 ml) containing hydrochloric acid (32% in water; 40 ml) and water (80 ml). During the addition the temperature of the reaction mixture is kept between 0° C. and 5° C. by means of an ice bath. After the addition is complete (0.5 hours), stirring is continued for 1 hour. The reaction mixture is then transferred into a dropping funnel and slowly added at −15° C. to a stirred solution of 2-cumyl-4-t-octylphenol (95%; 34.15, 100 mmol) in methanol/xylene (85:15; 200 ml) containing sodium hydroxide microprills (4 g, 100 mmol). During the addition, the temperature of the reaction mixture is kept between −15° C. and −5° C. by means of an isopropanol-dry ice bath; the pH is measured by means of an electrode and held above 7 by concomitant addition of sodium hydroxide (30% in water). After the addition is complete (1 hour), the cooling bath is removed and the suspension stirred overnight. The red suspension is filtered off and the residue solved in hot isopropanol. After cooling, the liquid is filtered an evaporated to dryness. The solid is dissolved in less hot ethyl acetate, precipitated with water.

Yield 33.1 g (63.8 mmol, 64%)

$^1$H-NMR (400 MHz, CDCl$_3$), δ (ppm): 13.02 (s broad, 1H), 9.51 (s broad, 1H), 9.48 (s broad, 1H), 7.77 (d, 1H), 7.64 (d like, 1H), 7.57 (d, 1H), 7.31-7.25 (m, 4H), 7.18-7.14 (m, 1H), 7.13 (d like, 1H), 1.86 (s, 2H), 1.83 (s, 6H), 1.51 (s, 6H), 0.84 (s, 9H).

Example 7

Preparation of Compound 5b

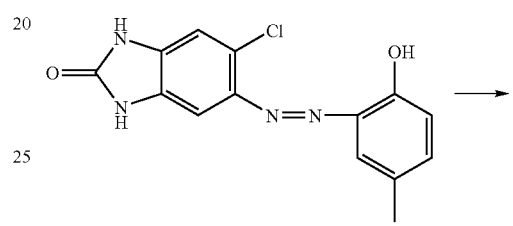

5a

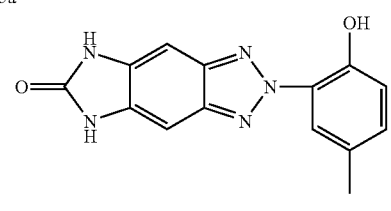

5b

A stirred mixture of compound 5a (96%; 20.0 g; 66 mmol), sodium azide (99%; 5.65 g; 85.8 mmol), copper(I) bromide (495 mg; 0.7 mmol) and 1-methyl-2-pyrrolidinone (75 ml) is heated to 150° C. The temperature is maintained and the progress of reaction is monitored by TLC (2 days). The dark solution is added to a stirred mixture of ice and water. The precipitate is filtered off and the filter cake is washed in a soxhlet apparatus with 600 ml of ethyl acetate for 3 days. Then the product is extracted from the thimble by another 3 days of soxhlet extraction with 500 ml dioxane. The dioxane extract is concentrated to the half, the product is precipitated by addition of water and dried.

Yield: 2.5 g (8.9 mmol, 13%)

Melting point: 300° C. decomposition $^1$H-NMR (300 MHz, DMSO-d$_6$), δ (ppm): 10.02 (s broad, 2H), 10.63 (s broad, 1H), 7.76-7.75 (d, 1H), 7.28 (s, 2H) 7.17-7.15 (dd, 1H), 7.04-7.02 (d, 1H), 2.31 (s, 3H).

UV-vis (dioxane), $\lambda_{max}$/nm (ε/dm$^3$ mol$^{-1}$ cm$^{-1}$): 355 (37735)

The above mentioned intermediate 5a is prepared as follows:

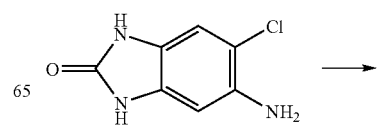

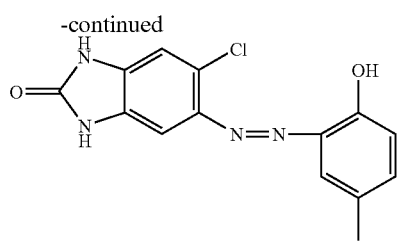

5a

Sodium nitrite (4 molar in water; 20 ml, 80 mmol) is slowly added between 0° C. and 5° C. to a stirred suspension of 5-amino-6-chloro-benzimidazol-2-one (13.77 g, 75 mmol) in acetic acid (200 ml) containing hydrochloric acid (32% in water; 20 ml) and water (40 ml). During the addition the temperature of the reaction mixture is kept between 0° C. and 5° C. by means of an ice bath. After the addition is complete (0.5 hours), stirring is continued for 1 hour. The reaction mixture is then transferred into a dropping funnel and slowly added at −15° C. to a stirred solution of p-cresol (99%; 8.19 g, 75 mmol) in methanol/xylene (85:15; 125 ml) containing sodium hydroxide microprills (3 g, 75 mmol). During the addition, the temperature of the reaction mixture is kept between −15° C. and −5° C. by means of an isopropanol-dry ice bath; the pH is measured by means of an electrode and held above 7 by concomitant addition of sodium hydroxide (30% in water). After the addition is complete (1 hour), the cooling bath is removed and the thick suspension stirred overnight. The suspension is filtered off and dried.

Yield 17.1 g (56.5 mmol, 73.3%; HPLC-MS: MW 301.9/ 95.6% Area UV)

Melting point: 290° C. decomposition

Example 8

Preparation of Compound 6b

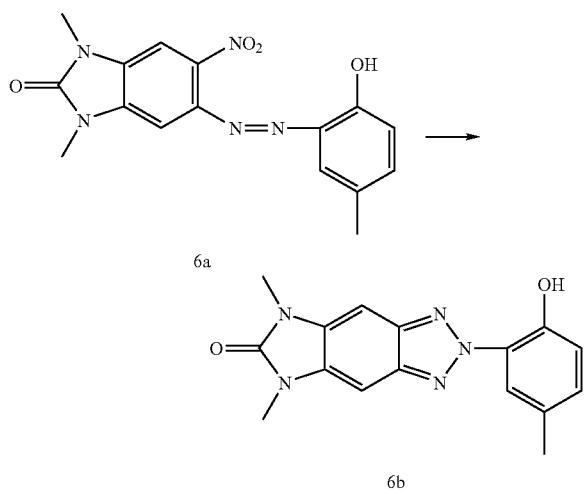

A stirred mixture of compound 6a (3.4 g; 10 mmol), sodium azide (99%; 0.85 g; 13 mmol) and 1-methyl-2-pyrrolidinone (25 ml) is heated to 160° C. The temperature is maintained and the progress of reaction is monitored by TLC (16 hours). The dark solution is added to a stirred mixture of ice and water. The residue is filtered off and the product is extracted from the residue by Soxhlet extraction with 400 ml ethyl acetate. After evaporation of the ethyl acetate the residue is suspended in 30% aqueous sodium hydroxide (50 ml) and ethanol (50 ml) and heated to reflux while stirring. After cooling to room temperature a 32% aqueous hydrogen chloride solution is added (30 ml) and the precipitate is filtered of. The procedure is repeated by refluxing the obtained residue in 30% aqueous sodium hydroxide (30 ml), ethanol (30 ml) and water (10 ml) and finally adding 32% aqueous hydrogen chloride solution (30 ml). The precipitate is filtered off, washed with water and dried.

Yield 0.82 g (26.5 mmol, 27%).

Melting point: 280° C.

UV-vis (dioxane), $\lambda_{max}$/nm ($\epsilon$/nm ($\epsilon$/dm$^3$ mol$^{-1}$ cm$^{-1}$): 357 (38187)

The above mentioned intermediate 6a is prepared as follows:

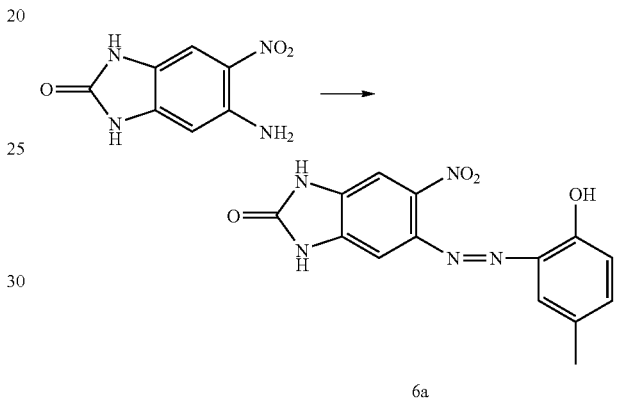

6a

Sodium nitrite (4 molar in water; 27.5 ml, 110 mmol) is slowly added between 0° C. and 5° C. to a stirred suspension of 5-amino-1,3-dimethyl-6-nitro-benzimidazol-2-one (22.2 g, 100 mmol) in acetic acid (250 ml) containing hydrochloric acid (32% in water; 25 ml) and water (50 ml). During the addition the temperature of the reaction mixture is kept between 0° C. and 5° C. by means of an ice bath. After the addition is complete (45 minutes), stirring is continued for 1 hour. The reaction mixture is then transferred into a dropping funnel and slowly added at −15° C. to a stirred solution of p-cresol (99%; 10.95 g, 100 mmol) in methanol (170 ml) containing sodium hydroxide microprills (4 g, 100 mmol). During the addition, the temperature of the reaction mixture is kept between −15° C. and −5° C. by means of an isopropanol-dry ice bath; the pH is measured by means of an electrode and held above 7 by concomitant addition of sodium hydroxide (30% in water; 350 ml). After the addition is complete (1 hour; end pH 6.3), the cooling bath is removed and the orange suspension stirred overnight. The suspension is filtered off, washed with water and dried.

Yield 31.4 g (95 mmol, 95%)

Melting point: 281° C.

Example 9

Preparation of Compound 7b CG45-0085 (FRK258/4)

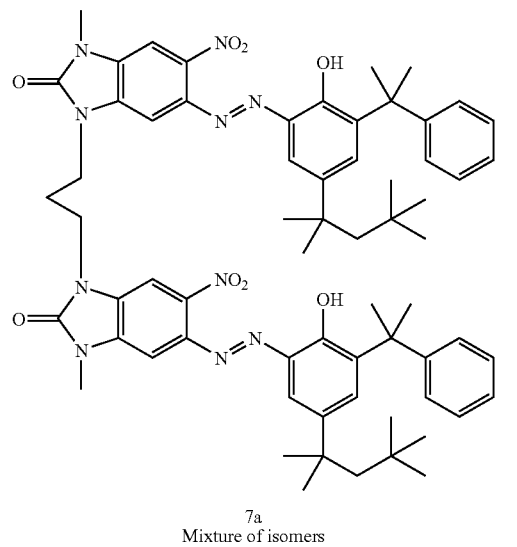

7a
Mixture of isomers

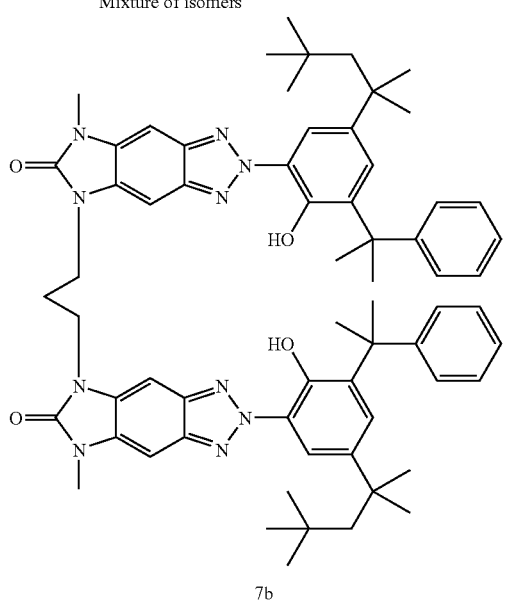

7b

A stirred mixture of crude compound 7a (20.0 g) prepared as described below, sodium azide (99%; 3.6 g, 55 mmol) and 1-methyl-2-pyrrolidinone (75 ml) is heated to 180° C. The temperature is maintained and the progress of reaction is monitored by TLC (6 hours). The dark solution is cooled over night to room temperature followed by the addition of water (100 ml) and toluene (300 ml). The organic phase is washed with water (1×50 ml), and the solvent evaporated. The residue is chromatographed on a silica gel column (hexane/ethyl acetate 1:1).

Yield 5.0 g (4.7 mmol, 26%)

Melting point: 263° C.

UV-vis (CHCl$_3$), $\lambda_{max}$/nm ($\epsilon$/dm$^3$ mol$^{-1}$ cm$^{-1}$): 363 (66017)

The above mentioned intermediate 7a is prepared as follows:

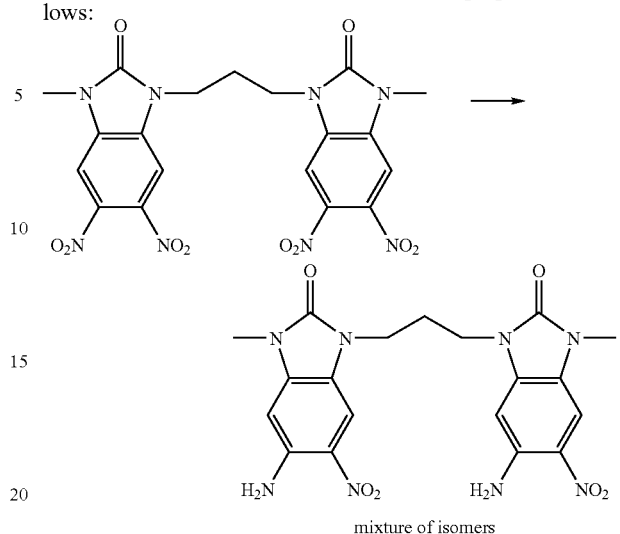

mixture of isomers

A steel reactor is charged with 1,1'-(1,3-propanediyl)bis[3-methyl-5,6dinitrobenzimidazol-2-one]*) (10.3 g; 20 mmol) and 100 ml of a 32% solution of ammonia in water. After stirring over night at 160° C. (pressure rises up to 20 bar) the reaction mixture is cooled to room temperature. The so formed diamino-dinitro-derivative is filtered off as an orange precipitate and washed with water.

Yield 7.9 g (1.1 mmol, 88%)

Melting point: 296° C. decomposition

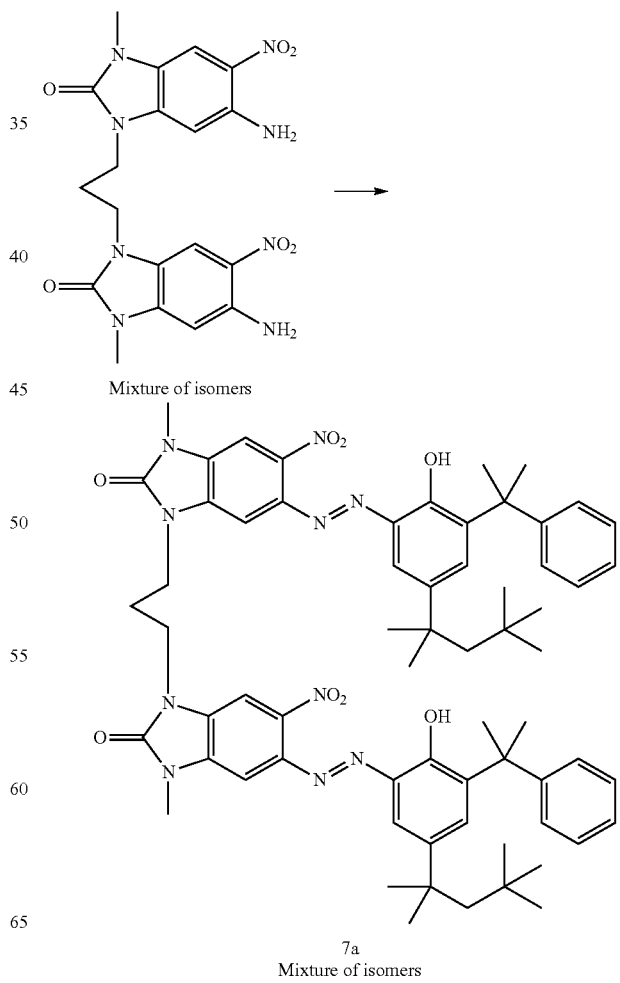

7a
Mixture of isomers

Sodium nitrite (4 molar in water; 10 ml, 40 mmol) is slowly added between 0° C. and 5° C. to a stirred solution of the above described diaminodinitro derivate (6.9 g, 15 mmol) in acetic acid (70 ml) and hydrochloric acid (32% in water; 10 ml). During the addition the temperature of the reaction mixture is kept between 0° C. and 5° C. by means of an ice bath. After the addition is complete (one hour), stirring is continued for 1.5 hours. The reaction mixture is then transferred into a dropping funnel and slowly added at −20° C. to a stirred solution of 2-cumyl-4-t-octylphenol (95%; 10.2 g, 30 mmol) in methanol/toluene (110 ml; 6:5) containing sodium hydroxide microprills (1.2 g, 30 mmol). During the addition, the temperature of the reaction mixture is kept between −20° C. and −5° C. by means of an isopropanol-dry ice bath; the pH is measured by means of an electrode and held above 7 by concomitant addition of sodium hydroxide (30% in water). After the addition is complete (1 hours; initial pH>11.0), the cooling bath is removed and the red suspension stirred overnight. After adding water (50 ml) and toluene (100 ml) The water phase is split off and washed with toluene (2×100 ml). The combined organic phases are washed with water, dried (Na$_2$SO$_4$), filtered and the solvent evaporated.

Yield 19.3 g (114%) crude

Melting point: 160-175° C. (mixture of isomers)

*) 1,1-(1,3-propanediyl)bis[3-methyl-5,6dinitrobenzimidazol-2-one] and corresponding o-nitro or o-chloro anilines can be prepared according to known procedures.

Example 10

Preparation of Compound 7c

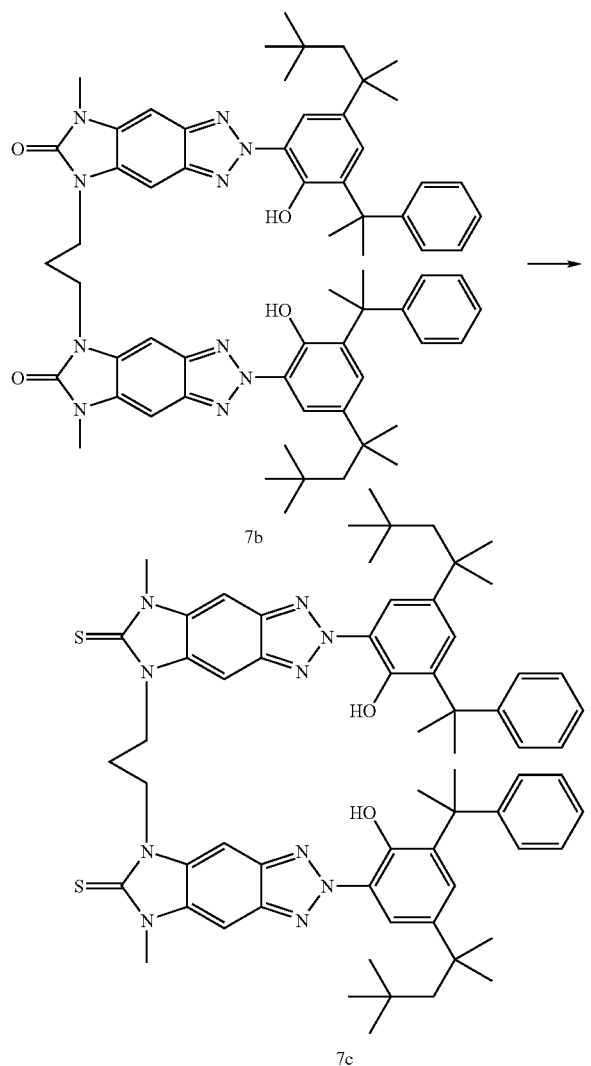

A stirred mixture of compound 7b (2.4 g, 2.25 mmol), Lawesson Reagent (98%; 5.46 g, 13.5 mmol) and xylene (20 ml) is heated to 130° C. The temperature is maintained and the progress of reaction is monitored by TLC (if necessary additional Lawesson Reagent is added). The reaction mixture is cooled to room temperature, filtered and evaporated. Followed by chromatography on a silica gel column (hexane/ethyl acetate 7:3) and the obtained product is recrystallized from acetone.

Yield 1.2 g (1.1 mmol, 50%)

Melting point: 183° C.

UV-vis (CHCl3), $\lambda_{max}$/nm ($\epsilon$/dm$^3$ mol$^{-1}$ cm$^{-1}$): 384 (98165)

Example 11

Preparation of Compound 8b

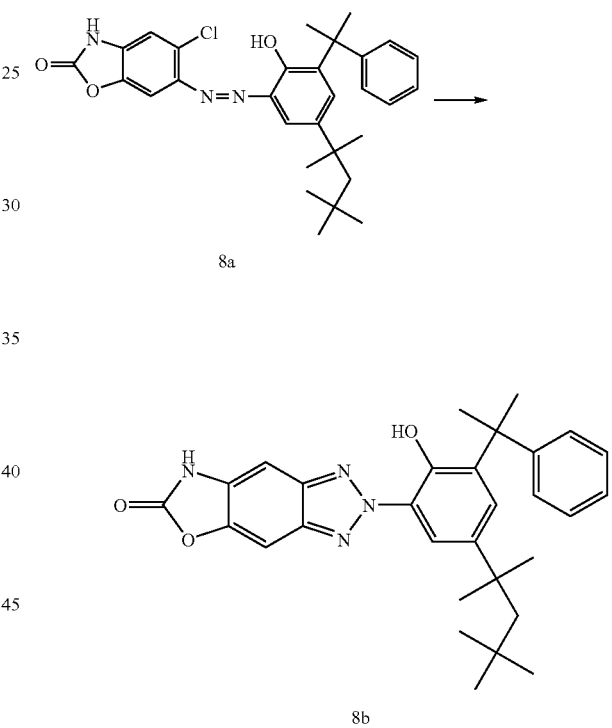

A stirred mixture of compound 8a (17.8 g; 34.2 mmol), sodium azide (99%; 2.9 g; 44.2 mmol), copper(I) bromide (0.5 g; 3.5 mmol) and 1-methyl-2-pyrrolidinone (150 ml) is heated to 120° C. The temperature is maintained and the progress of reaction is monitored by TLC (4 hours). The dark solution is added in a stirred mixture of ice and water. The residue is solved in ethyl acetate (150 ml). The water phase is split off and washed with ethyl acetate (1×50 ml). The combined organic phases are washed with brine, dried (Na$_2$SO$_4$), filtered and the solvent evaporated. The residue is chromatographed on a silica gel column (hexane/ethyl acetate 9:1)

Yield 10.7 g (21.5 mmol, 63%)

Melting point: 203° C.

UV-vis (CHCl$_3$), $\lambda_{max}$/nm ($\epsilon$/dm$^3$ mol$^{-1}$ cm$^{-1}$): 355 (22973)

The above mentioned intermediate 8a is prepared as follows:

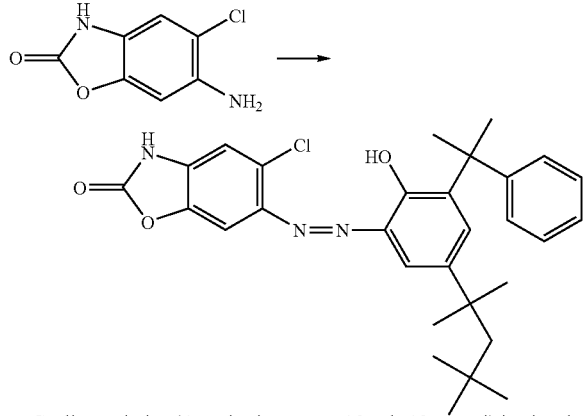

Sodium nitrite (4 molar in water; 10 ml, 40 mmol) is slowly added between 0° C. and 5° C. to a stirred solution of 6-amino-5-chloro-benzoxazol-2-one (5 g, 27 mmol) in acetic acid (50 ml) containing hydrochloric acid (32% in water; 15 ml) and water (10 ml). During the addition the temperature of the reaction mixture is kept between 0° C. and 5° C. by means of an ice bath.

After the addition is complete (30 minutes), stirring is continued for 1 hour. The reaction mixture is then transferred into a dropping funnel and slowly added at −15° C. to a stirred solution of 2-cumyl-4-t-octylphenol (95%; 8.8 g, 27 mmol) in methanol/xylene (120 ml 85:15) containing sodium acetate (2.2 g, 27 mmol). During the addition, the temperature of the reaction mixture is kept between −20° C. and −5° C. by means of an isopropanol-dry ice bath; the pH is measured by means of an electrode and held between 8, and 9 by concomitant addition of sodium hydroxide (30% in water). After the addition is complete (1 hour), the cooling bath is removed and the suspension stirred overnight. After adding water (200 ml) and ethyl acetate (300 ml), the water phase is split off and washed with ethyl acetate (3×50 ml). The combined organic phases are washed with brine, dried ($Na_2SO_4$), filtered and the solvent evaporated. The residue is suspended with hot methanol. The cold suspension is filtered off, washed with methanol and dried. Yield 7.2 g (13.8 mmol, 51%).

Melting point: 200° C.

Example 12

Preparation of Compound 8c

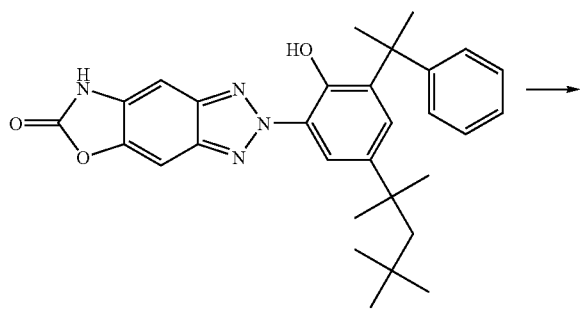

8b

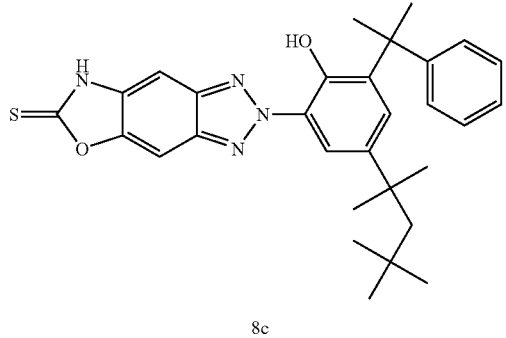

8c

A stirred mixture of compound 8b (1.0 g, 2 mmol), Lawesson Reagent (98%; 3.2 g, 7.9 mmol) and xylene (30 ml) is heated to 130° C. The temperature is maintained and the progress of reaction is monitored by TLC (if necessary additional Lawesson Reagent is added). The reaction mixture is cooled and filtered. The liquid layer is concentrated to dryness and the residue is chromatographed on a silica gel column (hexane/ethyl acetate 7:3)

Yield 0.8 g (1.4 mmol, 81%)

Melting point: 109° C.

UV-vis ($CHCl_3$ $\lambda_{max}$/nm ($\epsilon$/dm$^3$ mol$^{-1}$ cm$^{-1}$): 375 (44920)

Example 13

Preparation of Compound 9b

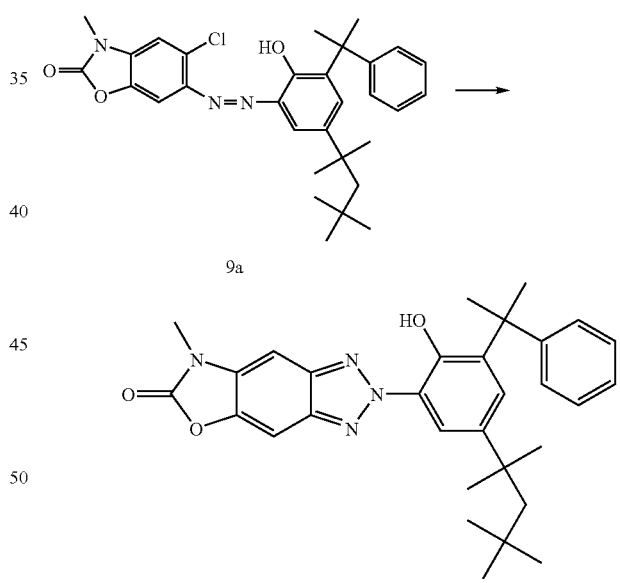

A stirred mixture of compound 9a (4.0 g; 7.5 mmol), sodium azide (99%; 2.9 g; 44.2 mmol), copper(I) bromide (0.11 g; 0.75 mmol) and 1-methyl-2-pyrrolidinone (50 ml) is heated to 120° C. The temperature is maintained and the progress of reaction is monitored by TLC (2 hours). The dark solution is added to a stirred mixture of ice and water. The residue is dissolved in ethyl acetate (150 ml). The water phase is split off and washed with ethyl acetate (1×50 ml). The combined organic phases are washed with brine, dried ($Na_2SO_4$), filtered and the solvent evaporated. The residue is chromatographed on a silica gel column (hexane/ethyl acetate 7:3)

Yield 2.2 g (4.3 mmol, 57%)
Melting point: 176° C.
UV-vis (CHCl$_3$), $\lambda_{max}$/nm ($\epsilon$/dm$^3$ mol$^{-1}$ cm$^{-1}$): 357 (25423)

The above mentioned intermediate 9a is prepared as follows:

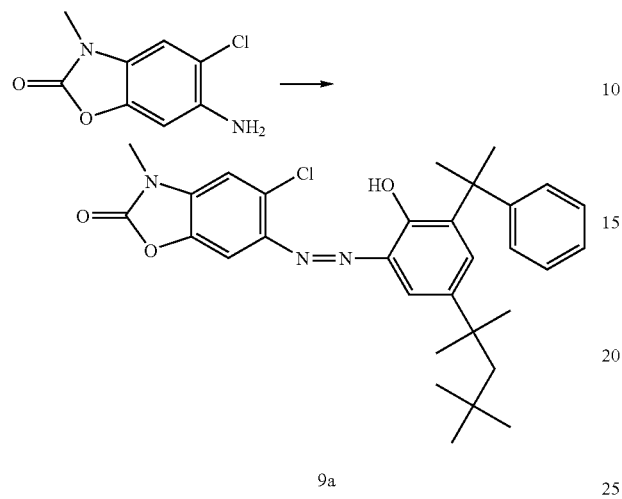

9a

Sodium nitrite (4 molar in water; 8 ml, 32 mmol) is slowly added between 0° C. and 5° C. to a stirred solution of 6-amino-5-chloro-3-methyl-benzoxazol-2-one (5.8 g, 29 mmol) in acetic acid (60 ml), hydrochloric acid (32% in water; 15 ml) and water (10 ml). During the addition the temperature of the reaction mixture is kept between 0° C. and 5° C. by means of an ice bath. After the addition is complete (30 minutes), stirring is continued for 1 hour. The reaction mixture is then transferred into a dropping funnel and slowly added at −15° C. to a stirred solution of 2-cumyl-4-t-octylphenol (95%; 9.4 g, 27.5 mmol) in methanol/xylene (100 ml 85:15) containing sodium acetate (2.4 g, 29 mmol). During the addition, the temperature of the reaction mixture is kept between −15° C. and −5° C. by means of an isopropanol-dry ice bath; the pH is measured by means of an electrode and held between 6 and 8 by concomitant addition of sodium hydroxide (30% in water). After the addition is complete (1 hour), the cooling bath is removed and the suspension stirred overnight. After adding brine (200 ml) and ethyl acetate (300 ml), the water phase is split off and washed with ethyl acetate (3×50 ml). The combined organic phases are washed with brine, dried (Na$_2$SO$_4$), filtered and the solvent evaporated. The residue is chromatographed on a silica gel column (hexane/ethyl acetate 6:2)

Yield 10.9 g (20.4 mmol, 70.4%)
Melting point: 231° C.

Example 14

Preparation of Compound 9c

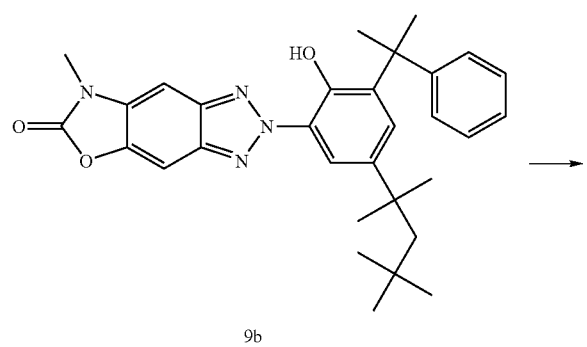

9b

-continued

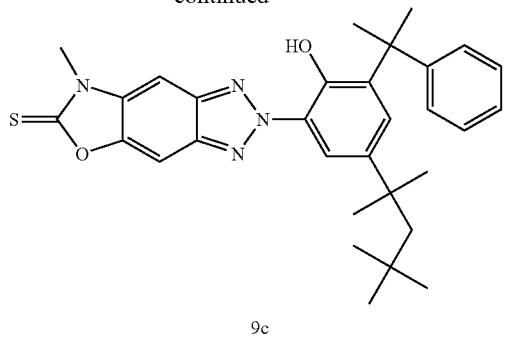

9c

A stirred mixture of compound 9b (1.0 g, 2 mmol), Lawesson Reagent (98%; 3.2 g, 7.9 mmol) and xylene (30 ml) is heated to 120° C. The temperature is maintained and the progress of reaction is monitored by TLC (if necessary additional Lawesson Reagent is added). The reaction mixture is cooled and filtered. The liquid layer is concentrated to dryness and the residue is crystallized with methanol.

Yield 0.8 g (1.5 mmol, 75%)
Melting point: 174° C.
UV-vis (CHCl$_3$), $\lambda_{max}$/nm ($\epsilon$/dm$^3$ mol$^{-1}$ cm$^{-1}$): 377 (43647)

Example 15

Preparation of Compound 10b

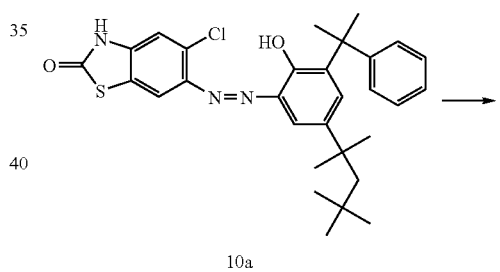

10a

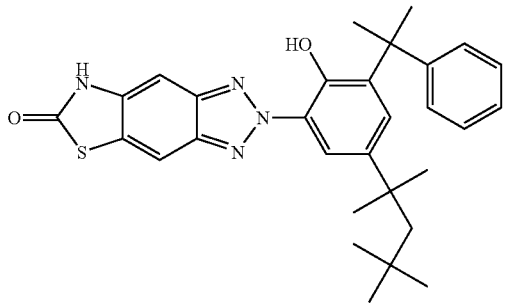

10b

A stirred mixture of compound 10a (10.0 g; 18.7 mmol), sodium azide (99%; 1.6 g; 24.2 mmol), copper(I) bromide (0.27 g; 1.9 mmol) and 1-methyl-2-pyrrolidinone (50 ml) is heated to 125° C. The temperature is maintained and the progress of reaction is monitored by TLC (8 hours). The dark solution is added in a stirred mixture of ice and water. The residue is solved in ethyl acetate (150 ml). The water phase is split off and washed with ethyl acetate (1×50 ml). The combined organic phases are washed with brine, dried (Na$_2$SO$_4$), filtered and the solvent evaporated. The residue is chromatographed on a silica gel column (cyclohexane/ethyl acetate 8:2)

Yield 3.3 g (6.4 mmol, 34%)
Melting point: 222° C.
UV-vis (CHCl$_3$), $\lambda_{max}$/nm ($\epsilon$/dm$^3$ mol$^{-1}$ cm$^{-1}$): 366 (27881)

The above mentioned intermediate 10a is prepared as follows:

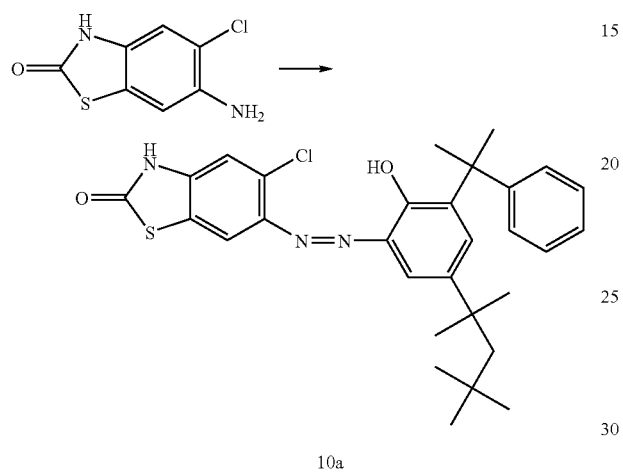

10a

Sodium nitrite (4 molar in water; 15 ml, 60 mmol) is slowly added between 0° C. and 5° C. to a stirred solution of 6-amino-5-chloro-benzothiazol-2-one (12.0 g, 60 mmol) in acetic acid (100 ml) containing hydrochloric acid (32% in water; 50 ml) and water (20 ml). During the addition the temperature of the reaction mixture is kept between 0° C. and 5° C. by means of an ice bath. After the addition is complete (60 minutes), stirring is continued for 1 hour. The reaction mixture is then transferred into a dropping funnel and slowly added at −15° C. to a stirred solution of 2-cumyl-4-t-octylphenol (95%; 20.5 g, 60 mmol) in methanol/xylene (150 ml 85:15) containing sodium acetate (4.9 g, 60 mmol). During the addition, the temperature of the reaction mixture is kept between −15° C. and −5° C. by means of an isopropanol-dry ice bath; the pH is measured by means of an electrode and held between 7 and 9 by concomitant addition of sodium hydroxide (30% in water). After the addition is complete (1 hour), the cooling bath is removed and the suspension stirred overnight. After adding water (200 ml) and ethyl acetate (500 ml), the water phase is split off and washed with ethyl acetate (3×50 ml). The combined organic phases are washed with brine, dried (Na$_2$SO$_4$), filtered and the solvent evaporated. The residue is suspended with cold methanol (0° C.). The cold suspension is filtered off, washed with cold methanol and dried. Yield 20.4 g (38.1 mmol, 64%).

Melting point: 253° C.

Example 16

Preparation of Compound 10c

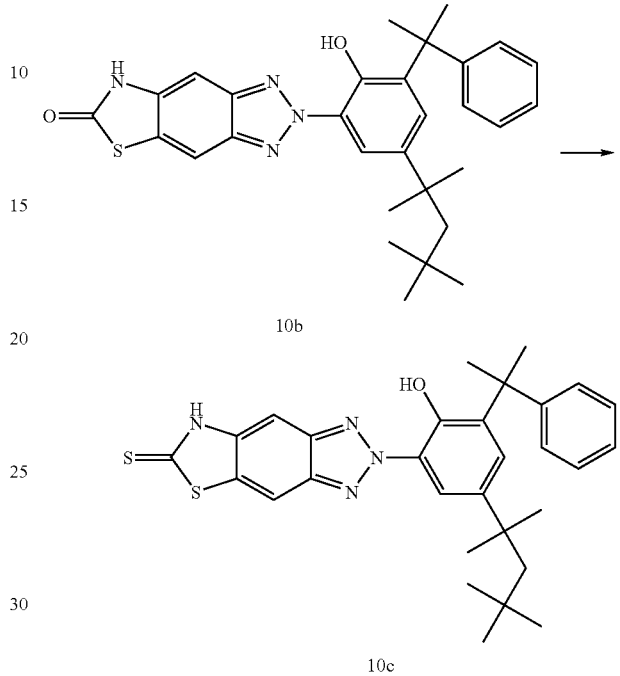

A stirred mixture of compound 10b (2.4 g, 4.7 mmol), Lawesson Reagent (98%; 7.8 g, 18.8 mmol) and xylene (40 ml) is heated to 120° C. The temperature is maintained and the progress of reaction is monitored by TLC (if necessary additional Lawesson Reagent is added). The reaction mixture is cooled and filtered. The liquid layer is concentrated to dryness and the residue is chromatographed on a silica gel column (hexane/ethyl acetate 85:15)

Yield 1.3 g (2.5 mmol, 53%)
Melting point: 254° C.
UV-vis (CHCl$_3$), $\lambda_{max}$/nm ($\epsilon$/dm$^3$ mol$^{-1}$ cm$^{-1}$): 390 (46882)

Example 17

Preparation of Compound 11b

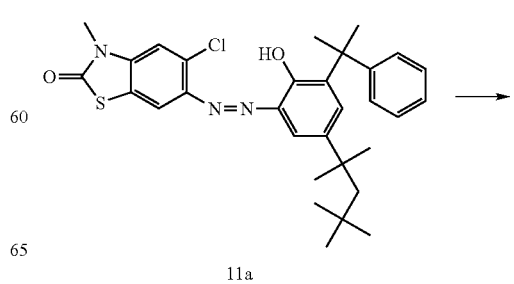

11a

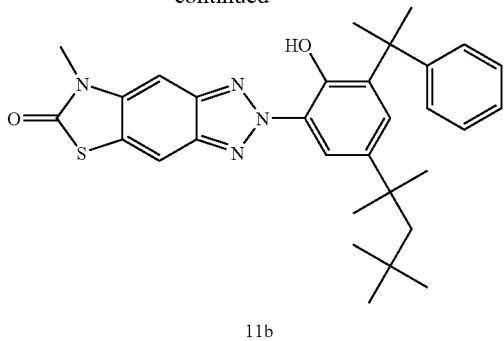

11b

A stirred mixture of compound 11a (20.0 g; 36.4 mmol), sodium azide (99%; 3 g; 46.2 mmol), copper(I) bromide (0.27 g; 1.9 mmol) and 1-methyl-2-pyrrolidinone (250 ml) is heated to 125° C. The temperature is maintained and the progress of reaction is monitored by TLC (4.5 hours). The dark solution is added in a stirred mixture of ice and water (1000 ml). The residue is filtered off and chromatographed on a silica gel column (cyclohexane/ethyl acetate 9.5:0.5)

Yield 16.1 g (30.5 mmol, 84%)

Melting point: 140° C.

UV-vis (CHCl$_3$), $\lambda_{max}$/nm ($\epsilon$/dm$^3$ mol$^{-1}$ cm$^{-1}$): 367 (27752)

The above mentioned intermediate 11a is prepared as follows:

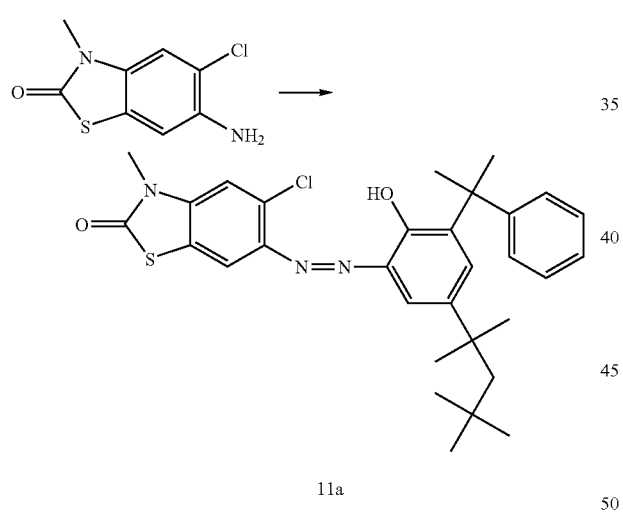

11a

Sodium nitrite (4 molar in water; 10 ml, 40 mmol) is slowly added between 0° C. and 5° C. to a stirred solution of 6-amino-5-chloro-3-methyl-benzothiazol-2-one (6.7 g, 31.2 mmol) in acetic acid (60 ml) containing hydrochloric acid (32% in water; 20 ml) and water (10 ml). During the addition the temperature of the reaction mixture is kept between 0° C. and 5° C. by means of an ice bath. After the addition is complete (45 minutes), stirring is continued for 1 hour. The reaction mixture is then transferred into a dropping funnel and slowly added at −10° C. to a stirred solution of 2-cumyl-4-t-octylphenol (11.5 g, 35 mmol) in methanol/xylene (120 ml; 85:15) containing sodium acetate (2.9 g, 35 mmol). During the addition, the temperature of the reaction mixture is kept between −15° C. and −5° C. by means of an isopropanol-dry ice bath; the pH is measured by means of an electrode and held between 8 and 9 by concomitant addition of sodium hydroxide (30% in water). After the addition is complete (1 hour), the cooling bath is removed and the suspension stirred overnight. After adding brine (100 ml) and ethyl acetate (300 ml), the water phase is split off and washed with ethyl acetate (3×50 ml). The combined organic phases are washed with brine, dried (Na$_2$SO$_4$), filtered and the solvent evaporated. The residue is suspended with cold methanol (0° C.). The cold suspension is filtered off, washed with cold methanol and dried. Yield 10.9 g (19.8 mmol, 57%).

Melting point: 255° C.

Example 18

Preparation of Compound 11c

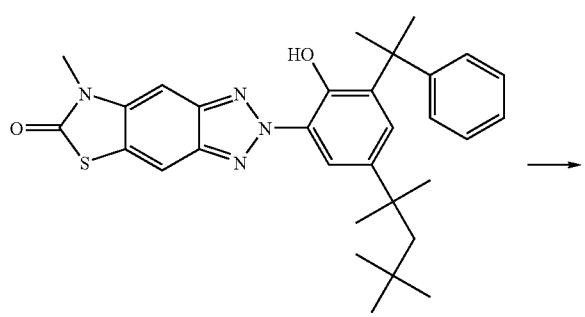

11b

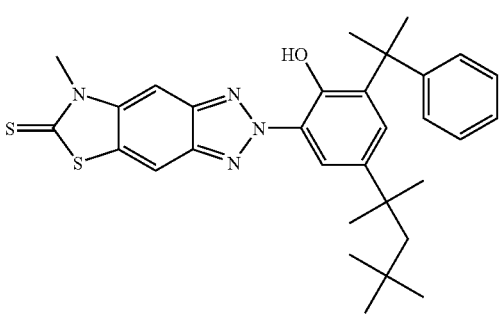

11c

A stirred mixture of compound 11b (1.31 g, 2.5 mmol), Lawesson Reagent (98%; 4.04 g, 10 mmol) and xylene (15 ml) is heated to 120° C. The temperature is maintained and the progress of reaction is monitored by TLC (2 hours) (if necessary additional Lawesson Reagent is added). The reaction mixture is cooled and filtered. The liquid layer is concentrated to dryness and the residue is chromatographed on a silica gel column (hexane/ethyl acetate 95:5)

Yield 1.15 g (2.1 mmol, 84%)

Melting point: 120° C.

UV-vis (CHCl$_3$), $\lambda_{max}$/nm ($\epsilon$/dm$^3$ mol$^{-1}$ cm$^{-1}$): 392 (46042)

Example 19

Preparation of Compound 12b

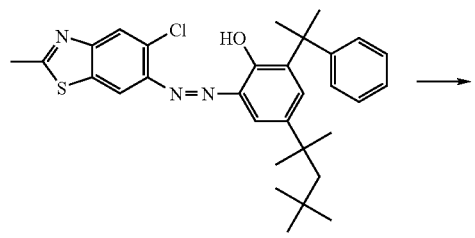

12a

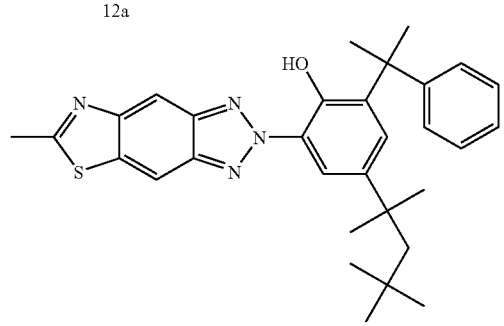

12b

A stirred mixture of compound 12a (5.35 g; 10 mmol), sodium azide (99%; 0.85 g; 13 mmol), copper(I) bromide (0.19 g; 1.3 mmol) and 1-methyl-2-pyrrolidinone (100 ml) is heated to 60° C. The temperature is maintained and the progress of reaction is monitored by TLC (1.5 hours). The dark solution is added in water (100 ml) and ethyl acetate (250 ml). The water phase is split off and washed with ethyl acetate (2×50 ml). The combined organic phases are washed with brine, dried ($Na_2SO_4$), filtered and the solvent evaporated. The residue is chromatographed on a silica gel column (hexane/ethyl acetate 4:1) and crystallized with hexane.

Yield 2.65 g (5.2 mmol, 52%)
Melting point: 188° C.
UV-vis ($CHCl_3$), $\lambda_{max}$/nm ($\epsilon$/$dm^3$ $mol^{-1}$ $cm^{-1}$): 364 (22533)

The above mentioned intermediate 12a is prepared as follows:

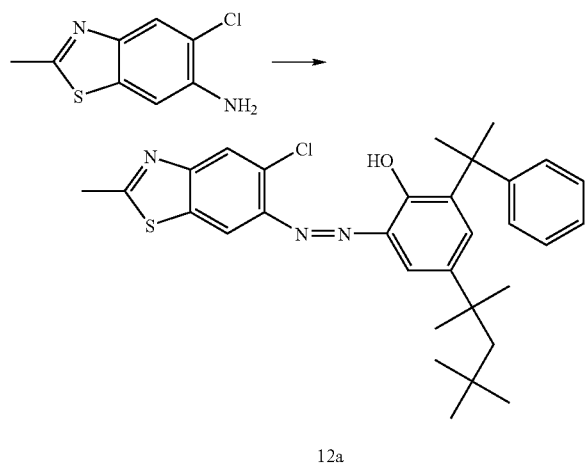

12a

Sodium nitrite (4 molar in water; 10 ml, 40 mmol) is slowly added between 0° C. and 5° C. to a stirred solution of 5-chloro-2-methyl-benzothiazol-6-ylamine (7.2 g, 31.2 mmol) in acetic acid (50 ml) containing hydrochloric acid (32% in water; 12 ml) and water (25 ml). During the addition the temperature of the reaction mixture is kept between 0° C. and 5° C. by means of an ice bath. After the addition is complete (45 minutes), stirring is continued for 1 hour. The reaction mixture is then transferred into a dropping funnel and slowly added at −10° C. to a stirred solution of 2-cumyl-4-t-octylphenol (11.5 g, 35 mmol) in methanol/xylene (120 ml; 85:15) containing sodium acetate (4.7 g, 56 mmol) and sodium hydroxide microprills (1.4 g; 35 mmol). During the addition, the temperature of the reaction mixture is kept between −15° C. and −5° C. by means of an isopropanol-dry ice bath; the pH is measured by means of an electrode and held between 7 and 9 by concomitant addition of sodium hydroxide (30% in water; 100 ml). After the addition is complete (1 hour), the cooling bath is removed and the suspension stirred overnight. After adding brine (100 ml) and dichloromethane (300 ml), the water phase is split off and washed with dichloromethane (2×50 ml). The combined organic phases are washed with brine, dried ($Na_2SO_4$), filtered and the solvent evaporated. The residue is recrystallized from methanol (500 ml). Yield 12.4 g (23.2 mmol, 66%).

Melting point: 206° C.

Example 20

Preparation of Compound 13b

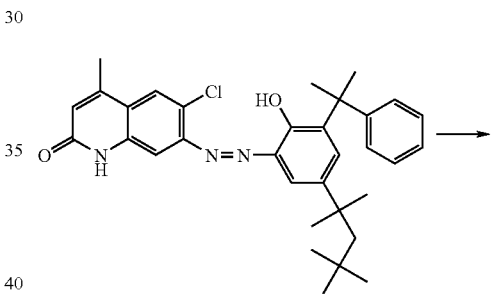

13a

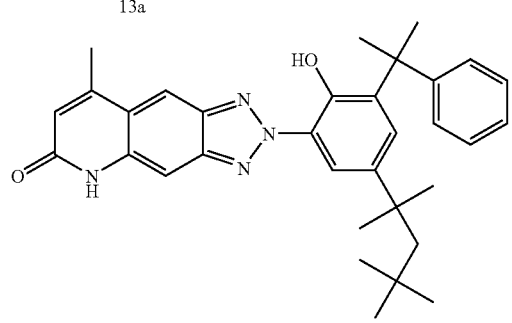

13b

A stirred mixture of compound 13a (5.45 g; 10 mmol), sodium azide (99%; 0.85 g; 13 mmol), copper(I) bromide (0.23 g; 1.6 mmol) and methyl sulfoxide (20 ml) is heated to 70° C. The temperature is maintained and the progress of reaction is monitored by TLC (0.5 hours). The dark solution is added in water (200 ml) and filtered off. The residue is suspended in hot isopropanol (25 ml; 0.5 hours). After the suspension is cooled, the residue is filtered off and dried.

Yield 4.6 g (8.7 mmol, 87%)
Melting point: 300° C.
UV-vis (dioxane), $\lambda_{max}$/nm ($\epsilon$/$dm^3$ $mol^{-1}$ $cm^{-1}$): 398 (40539), 419 (33575)

The above mentioned intermediate 13a is prepared as follows:

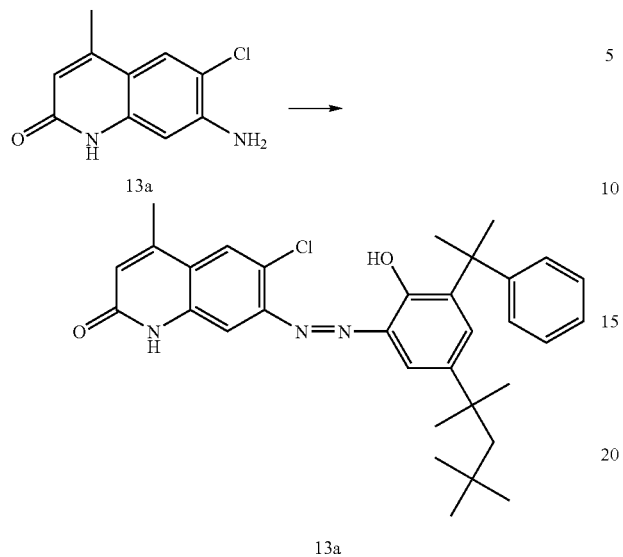

13a

Sodium nitrite (4 molar in water; 25 ml, 100 mmol) is slowly added between 0° C. and 5° C. to a stirred solution of 5-amino-6-chloro-4-methyl-2-chinolone (20.9 g, 100 mmol) in acetic acid (150 ml) containing hydrochloric acid (37% in water; 35 ml) and water (150 ml). During the addition the temperature of the reaction mixture is kept between 0° C. and 5° C. by means of an ice bath. After the addition is complete (30 minutes), stirring is continued for 1 hour. The reaction mixture is then transferred into a dropping funnel and slowly added at −15° C. to a stirred solution of 2-cumyl-4-t-octylphenol (32.5 g, 100 mmol) in methanol/xylene (200 ml; 85:15) containing sodium acetate (13.2 g, 160 mmol) and sodium hydroxide microprills (2.0 g; 50 mmol). During the addition, the temperature of the reaction mixture is kept between −15° C. and −5° C. by means of an isopropanol-dry ice bath; the pH is measured by means of an electrode and held between 7 and 12 by concomitant addition of sodium hydroxide (30% in water; 150 ml). After the addition is complete (1 hour), the cooling bath is removed and the suspension stirred overnight. The residue is filtered off, washed with water and dried.

Yield 44.3 g (84.5 mmol, 85%).
Melting point: 299° C.

Example 21

Preparation of Compound 14b

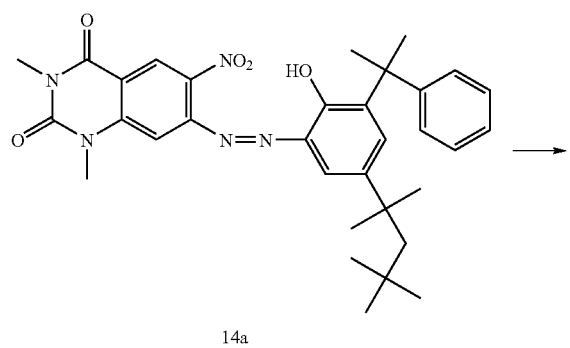

14a

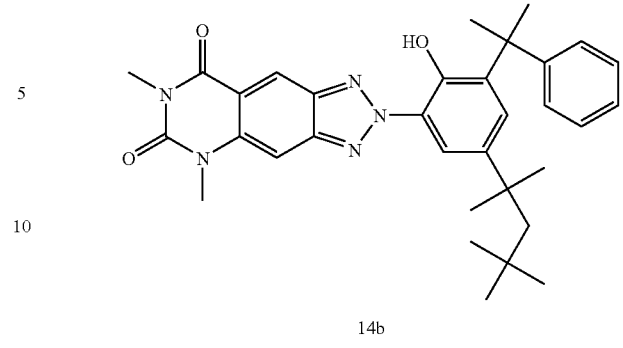

14b

A stirred mixture of compound 14a (16.6 g; 28 mmol), sodium azide (99%; 2.4 g; 39 mmol) and 1-methyl-2-pyrrolidinone (100 ml) is heated to 130° C. The temperature is maintained and the progress of reaction is monitored by TLC (16 hours). The dark solution is poured onto ice (200 g), extracted with toluene (2×100 ml) and ethyl acetate (3×100 ml) and the collected organic phases are evaporated. The resulting 25 g of red oil are chromatographed on a silica gel column (ethyl acetate/hexane 2:8) to yield 3.6 g of a solid which is purified again by semi preparative LC.

Yield 1.6 g (2.9 mmol, 10%)
Melting point: 209° C.
UV-vis (CHCl$_3$), $\lambda_{max}$/nm ($\epsilon$/dm$^3$ mol$^{-1}$ cm$^{-1}$): 391 (20670)

The above mentioned intermediate 14a is prepared as follows:

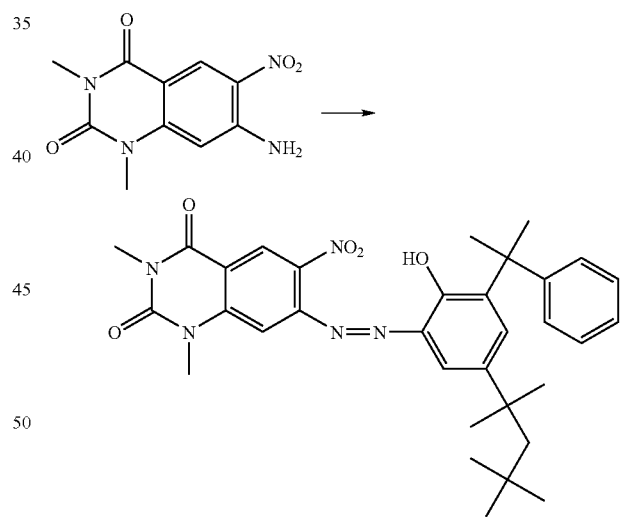

14a 7-amino-1,3-dimethyl-6-nitro-quinazoline-2,4-dione (7.0 g, 28 mmol) are dissolved in concentrated sulfuric acid (40 ml) and added dropwise to nitrosylsulfuric acid (40% in sulfuric acid; 9.8 g, 31 mmol). During the addition the temperature of the reaction mixture is kept between 0° C. and 5° C. by means of an ice bath. After the addition is complete (30 minutes), stirring is continued for another hour. The reaction mixture is then transferred into a dropping funnel and slowly added at −10° C. to −15° C. to a stirred solution of 2-cumyl-4-t-octylphenol (9.1 g, 28 mmol) in methanol/m-xylene (50/50 by volume; 200 ml) containing sodium hydroxide microprills (1.15 g, 28 mmol). During the addition, the temperature of the reaction mixture is kept between −15° C. and −5° C. by means of an isopropanol-dry ice bath; the pH is measured by means of an electrode (initial pH>11) and later held between 5 and 8 by concomitant addition of sodium hydroxide (30% in water). After the addition is complete the cooling bath is removed and the suspension stirred overnight. Water (100 ml), brine (100 ml) and ethyl acetate (250 ml) are added, the water phase split off and washed with ethyl acetate (2×250 ml). The combined organic phases are washed with brine (200 ml), dried (Na$_2$SO$_4$), filtered and the solvent evaporated. The residue is chromatographed on a silica gel column (ethyl acetate/hexane 2:8).

Yield 24.0 g (6.8 mmol, 24%).

Melting point: 194° C. decomposition

Example 22

Preparation of Structure 15b

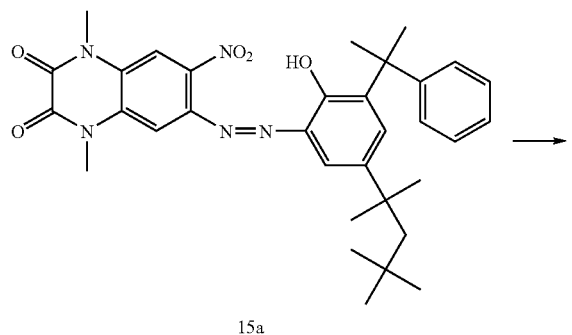

15a

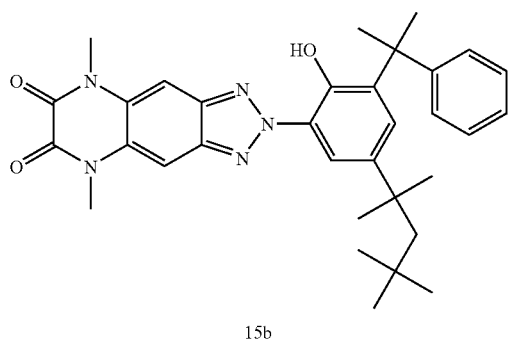

15b

A stirred mixture of compound 15a (6.0 g; 10 mmol), sodium azide (99%; 0.98 g; 15 mmol) and 1-methyl-2-pyrrolidinone (60 ml) is heated to 130° C. The temperature is maintained and the progress of reaction is monitored by TLC (3 hours). After pouring the reaction mixture onto ice (100 g), the crude product is filtered off and recrystallised from 1-methyl-2-pyrrolidinon.

Yield 1.6 g (2.9 mmol, 29%)

Melting point: 271° C.

UV-vis (CHCl$_3$), $\lambda_{max}$/nm ($\epsilon$/dm$^3$ mol$^{-1}$ cm$^{-1}$): 382 (36555)

The above mentioned intermediate 15a is prepared as follows:

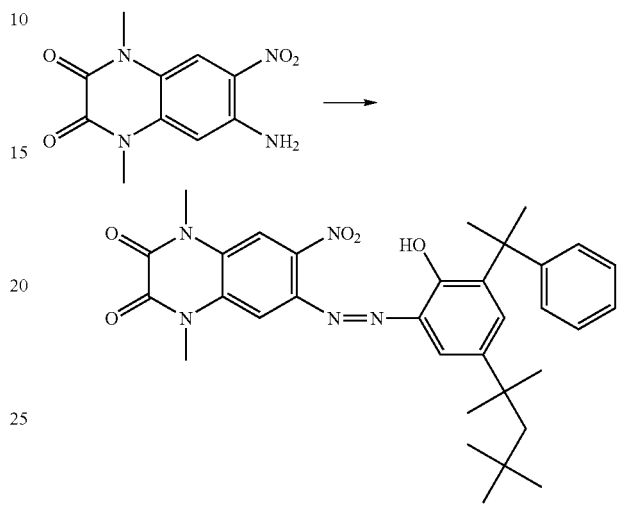

15a

Nitrosylsulfuric acid (40% in sulfuric acid; 5.6 g, 18 mmol) is added dropwise to a solution of 6-amino-1,4-dimethyl-7-nitro-1,4-dihydro-quinoxaline-2,3-dione (4.0 g, 16 mmol) in concentrated sulfuric acid (20 ml). During the addition the temperature of the reaction mixture is kept between 0° C. and 5° C. by means of an ice bath. After the addition is complete (30 minutes), stirring is continued over night at room temperature. The reaction mixture is cooled again with an ice bath, diluted with 25 g ice and then transferred into a dropping funnel and slowly added at −10° C. to −15° C. to a stirred solution of 2-cumyl-4-t-octylphenol (5.5 g, 16 mmol) in methanol/m-xylene (50/50 by volume; 200 ml) containing sodium hydroxide microprills (0.7 g, 16 mmol). During the addition, the temperature of the reaction mixture is kept between −15° C. and −10° C. by means of an isopropanol-dry ice bath; the pH is measured by means of an electrode (initial pH>11) and later held between 5 and 8 by concomitant addition of sodium hydroxide (30% in water). After the addition is complete the cooling bath is removed and the suspension stirred overnight. Water (100 ml), brine (100 ml) and ethyl acetate (250 ml) are added, the water phase split off and washed with ethyl acetate (2×250 ml). The combined organic phases are washed with brine (200 ml), dried (Na$_2$SO$_4$), filtered and the solvent evaporated. The residue is chromatographed on a silica gel column (ethyl acetate/hexane 1:1).

Yield 4.7 g (8.0 mmol, 50%).

Melting point: 190° C. decomposition

65

The mentioned ortho-nitroaniline can be prepared according to known procedures.

Example 23

Preparation of Structure 16b

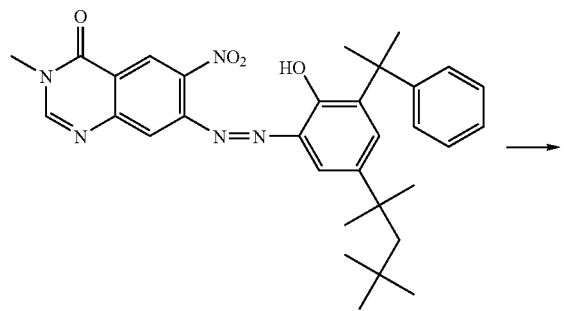

16a

↓

16b

A stirred mixture of compound 16a (0.8 g; 1.4 mmol), sodium azide (99%; 0.13 g; 2.0 mmol) and 1-methyl-2-pyrrolidinone (20 ml) is heated to 130° C. The temperature is maintained and the progress of reaction is monitored by TLC (5 hours). The dark solution is poured onto ice (50 g), extracted with ethyl acetate (3×20 ml), the combined organic phases are washed with brine (2×30 ml), dried ($Na_2SO_4$), filtered and the solvent evaporated. The residue is chromatographed on a silica gel column (ethyl-acetate/hexane 7/3) to yield 0.43 g solid which is purified again by semi preparative LC.

Yield 0.06 g (0.1 mmol, 8%)

Melting point: 208° C.

UV-vis ($CHCl_3$), $\lambda_{max}$/nm ($\epsilon$/dm$^3$ mol$^{-1}$ cm$^{-1}$): 388 (20880)

The above mentioned intermediate 16a is prepared as follows:

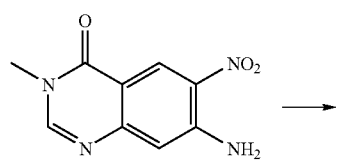

66

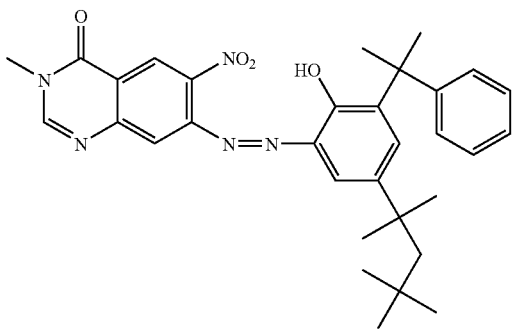

16a

Nitrosylsulfuric acid (40% in sulfuric acid; 3.5 g, 11 mmol) is added dropwise to a solution of 7-amino-3-methyl-6-nitro-3H-quinazolin-4-one (2.0 g, 10 mmol) in concentrated sulphuric acid (30 ml). During the addition the temperature of the reaction mixture is kept between 0° C. and 5° C. by means of an ice bath. After the addition is complete (30 minutes), stirring is continued for another two hours at room temperature. Then the reaction mixture is cooled again with an ice bath, diluted with 25 g ice, transferred into a dropping funnel and slowly added at −10° C. to −15° C. to a stirred solution of 2-cumyl-4-t-octylphenol (3.4 g, 10 mmol) in methanol/m-xylene (50/50 by volume; 100 ml) containing sodium hydroxide micropills (0.6 g, 15 mmol) and sodium acetate (8 g, 100 mmol). During the addition, the temperature of the reaction mixture is kept between −15° C. and −10° C. by means of an isopropanol-dry ice bath; the pH is measured by means of an electrode (initial pH>11) and later held between 5 and 8 by concomitant addition of sodium hydroxide (30% in water). After the addition is complete the cooling bath is removed and the suspension stirred overnight. Water (100 ml), brine (100 ml) and ethyl acetate (200 ml) are added, the water phase split off and washed with ethyl acetate (2×100 ml). The combined organic phases are washed with brine (2×100 ml), dried ($Na_2SO_4$), filtered and the solvent evaporated. The residue is chromatographed on a silica gel column (ethyl acetate/hexane 1:1).

Yield 0.32 g (0.6 mmol, 6%)

Melting point: 236° C. decomposition

The mentioned ortho-nitroaniline can be prepared according to known procedures.

B) APPLICATION EXAMPLES

Materials Used

| | Acryl/Melamine Clearcoat formulation: | |
|---|---|---|
| a) | Viacryl ® SC 303[1] (65% solution in xylene/butanol, 26:9 wt./wt.) | 27.51 g |
| b) | Viacryl ® SC 370[2] (75% in Solvesso 100[3]) | 23.34 g |
| c) | Maprenal ® MF 650[4] (55% in isobutanol) | 27.29 g |
| d) | Butylacaetate/butanol (37:8 wt./wt.) | 4.33 g |
| e) | Isobutanol | 4.87 g |
| f) | Solvesso ® 150[5] | 2.72 g |

-continued

| Acryl/Melamine Clearcoat formulation: | | |
|---|---|---|
| g) | Crystal oil 30[6] | 8.74 g |
| h) | Baysilone ® MA[7] (1% in Solvesso ® 150) | 1.20 g |
| | Total | 100.00 g |

Binder raw materials:
[1]Viacryl ® SC 303: acrylic resin (Solutia, formerly Vianova Resins)
[2]Viacryl ® SC 370: acrylic resin (Solutia, formerly Vianova Resins)
[3]Solvesso ® 100: aromatic hydrocarbon, bp. 163-180° C. (Exxon Corp.)
[4]Maprenal ® MF 650: melamine resin (Solutia, formerly Vianova Resins)
[5]Solvesso ® 150: aromatic hydrocarbon, bp. 180-203° C. (Exxon Corp.)
[6]Crystal-oil 30: aliphatic hydrocarbon; bp. 145-200° C. (Shell Corp.)
[7]Baysilone ® MA: leveling agent (Bayer AG)

UV-Absorbers and Other Stabilizers
Tinuvin 384®

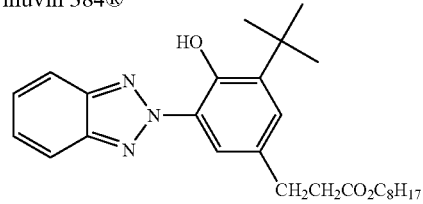

(commercial UV-Absorber from Ciba Specialty Chemicals)

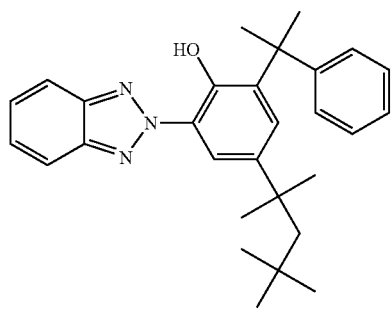

Tinuvin 928®
(commercial UV-absorber from Ciba Specialty Chemicals)
Tinuvin 400®

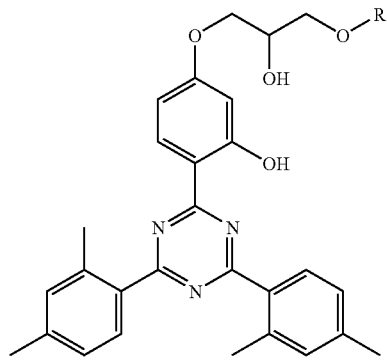

(commercial UV-Absorber from Ciba Specialty Chemicals)
Tinuvin 109®

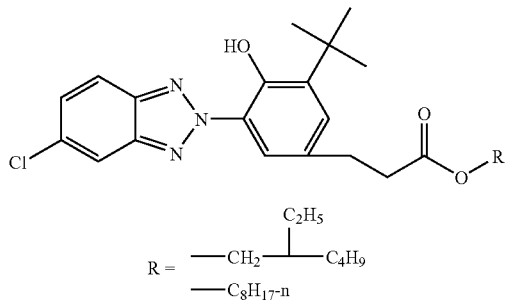

(commercial UV-absorber from Ciba Specialty Chemicals)
Oxanilide-1

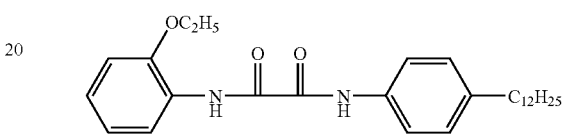

Compounds 1b and 3d (II)-(V) of example A1 and A3 are UV-absorbers according to the invention.
Tinuvin 152® (hindered amine stabilizer from Ciba Specialty Chemicals)

Example B1

Photo Permanence of UV-Absorbers

The photo permanence of the UV-absorbers is evaluated as follows:
the UV-absorbers of the present invention are incorporated into a thermosetting acryl/melamine clear coat (based on Viacryl® SC 303/Viacryl® SC 370/Maprenal® MF 650) in a concentration of 3% based on the solids content of the formulation (solids content: 50.4%). The clear coat is sprayed onto glass plates resulting in a dry film thickness of the clear coat of 20 μm after cure (130° C./30').

Prior to exposure of the specimens, the UV-absorption spectra are recorded using a UV/VIS spectrometer (Perkin Elmer, Lambda 40). Reference: unstabilized acryl/melamine clear coat. Subsequently the specimens are exposed in a Xenon WOM wetherometer (Atlas Corp.) according to SAE J 1960. The percentage of UV-absorber retained (determined at λ max) upon exposure is monitored by recording the UV-absorption spectra after regular exposure intervals. The test results are summarized in Table 1:

TABLE 1 photo permanence of claimed UV-absorbers during Xe-WOM exposure in comparison to commercial references

| | % UV-absorber retained after . . . hours Xe-WOM exposure | | | | |
|---|---|---|---|---|---|
| Sample | 1000 | 1500 | 2000 | 3000 | 4000 h |
| compound 14b | 94.6 | 92.4 | 83.2 | 73.3 | 63.1 |
| hydroxy-phenyl-benzotriazole[1] | 68.3 | 50.8 | 40.2 | 18.7 | n.a. |
| hydroxy-phenyl-benzotriazole[2] | 83.0 | n.a. | 68.2 | 43.4 | n.a |

TABLE 1-continued photo permanence of claimed UV-absorbers during Xe-WOM exposure in comparison to commercial references

| Sample | % UV-absorber retained after . . . hours Xe-WOM exposure | | | | |
|---|---|---|---|---|---|
| | 1000 | 1500 | 2000 | 3000 | 4000 h |
| hydroxy-phenyl-triazine[3] | 89.8 | 82.1 | 76.0 | 59.4 | n.a. |
| Oxanilide-1 | 8 | | | | |

[1] Tinuvin 384
[2] Tinuvin 928
[3] Tinuvin 400

Example B 2

In a second example two subsequent clear coats are applied on top of each other. The first clear coat (Clear coat I) is stabilized and applied as described in greater detail in example 1. A second thermosetting acryl/melamine clear coat (based on Viacryl® SC 303/Viacryl® SC 370/Maprenal® MF 650) is subsequently sprayed onto the first clear coat resulting in a dry film thickness of the second clear coat (clear coat II) of 40 μm after cure (130° C./30'). The second clear coat is stabilized using a UV-absorber combination of 3% Tinuvin 109/1.5% Tinuvin 400 and 1% Tinuvin 152 as co-stabilizer (HALS). Reference: unstabilized first clear coat. As described in example 1, the UV-transmission spectra are recorded prior to exposure of the specimens using a UV/VIS spectrometer (Perkin Elmer, Lambda 40). Subsequently the specimens are exposed in a Xenon WOM wetherometer (Atlas Corp.) according to SAE J 1960. The transmission values (determined at 396 nm) as a function of the exposure period are monitored by recording the transmission spectra after regular exposure intervals. The test results are summarized in Table 2:

TABLE 2 transmission values (determined at 396 nm) as a function of exposure intervals during Xe-WOM exposure

| Sample | transmission values (%) after . . . hours | | | | |
|---|---|---|---|---|---|
| | initial | 1000 | 2000 | 3000 | 4000 |
| Clear coat I: unstabilized Clear coat II: 3% Tinuvin 109/ 1.5% Tinuvin 400 | 21.3 | 24.3 | 25.4 | 26.4 | 28.1 |
| Clear coat I: 3% compound 14b Clear coat II: 3% Tinuvin 109/ 1.5% Tinuvin 400 | 0.35 | 0.38 | 0.46 | 0.62 | 0.74 |

The invention claimed is:

1. A compound of formula (I) or formula (IV)

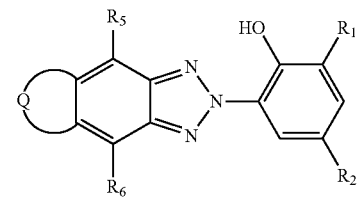

(I)

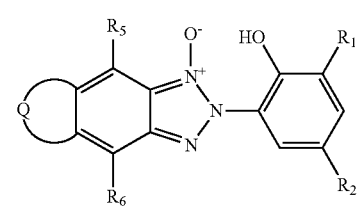

(IV)

wherein

Q is a heterocyclic radical forming a 5 or 6-membered ring together with the annealed phenyl-ring, which radical is selected from the group consisting of

wherein $X_{10}$ is O═C, S═C, $R_{101}$N, S(O)$_n$ where n is 0, 1 or 2;
$Y_{10}$ is $NR_{101}$, O, S(O)$_n$ where n is 0, 1 or 2;
$Z_{10}$ is O═C, S═C, $R_{101}$N, O, S(O)$_n$ where n is 0, 1 or 2;

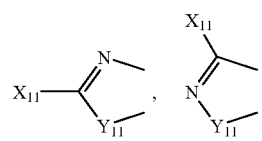

wherein $X_{11}$ is $R_{101}$, $N(R_{101})_2$, $OR_{101}$, $S(O)_nR_{101}$ where n is 0, 1 or 2;
$X_{11}'$ is $R_{101}$, $N(R_{101})_2$, $S(O)_nR_{101}$ where n is 0, 1 or 2;
$Y_{11}$ is C═O, $NR_{101}$, O, or S(O)$_n$ where n is 0, 1 or 2;

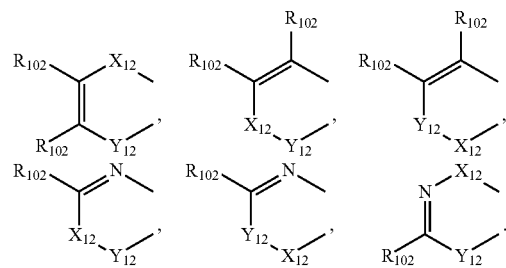

wherein
X$_{12}$ is C=O or C=S;
Y$_{12}$ is NR$_{101}$, O or S;

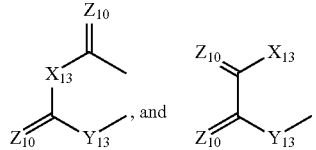

wherein
X$_{13}$ and Y$_{13}$ are independently NR$_{101}$, O or S;
each Z$_{10}$ is independently from each other O or S;
R$_{101}$ is hydrogen, straight or branched chain C$_1$-C$_{24}$alkyl, straight or branched chain C$_2$-C$_{18}$alkenyl, C$_2$-C$_6$ alkinyl, C$_5$-C$_{12}$cycloalkyl, phenyl, naphthyl or C$_7$-C$_{15}$phenylalkyl; or said straight or branched chain C$_1$-C$_{24}$ alkyl, straight or branched chain C$_2$-C$_{24}$ alkenyl, C$_5$-C$_{12}$ cycloalkyl, C$_2$-C$_6$ alkinyl substituted by one or more -halogen, —OH, —OR$_{22}$, —NH$_2$, —NHR$_{22}$, —N(R$_{22}$)$_2$, —NHCOR$_{23}$, —NR$_{22}$COR$_{23}$, —OCOR$_{24}$, —COR$_{25}$, —SO$_2$R$_{26}$, —SO$_3^-$M$^+$, —PO(R$_{27}$)$_n$(R$_{28}$)$_{2-n}$; —Si(R$_{29}$)$_n$(R$_{30}$)$_{3-n}$, —Si(R$_{22}$)$_3$, —N$^+$(R$_{22}$)$_3$ A$^-$, —S$^+$(R$_{22}$)$_2$ A$^-$ or combinations thereof; said straight or branched chain unsubstituted or substituted C$_1$-C$_{24}$ alkyl, straight or branched chain unsubstituted or substituted C$_2$-C$_{24}$ alkenyl, C$_5$-C$_{12}$ cycloalkyl or C$_2$-C$_6$ alkinyl interrupted by one or more —O—, —S—, —NH— or —NR$_{22}$— groups or combinations thereof;
said phenyl, naphthyl or C$_7$-C$_{15}$phenylalkyl can also be substituted by one or more -halogen, —CF$_3$, —NO$_2$, —NHR$_{22}$, —N(R$_{22}$)$_2$, —SO$_2$R$_{26}$, —PO(R$_{27}$)$_n$(R$_{28}$)$_{2-n}$, —OH, —OR$_{22}$, —COR$_{25}$, —R$_{25}$;
wherein
n is 0, 1 or 2;
R$_{22}$ is straight or branched chain C$_1$-C$_{18}$ alkyl, straight or branched chain C$_2$-C$_{18}$ alkenyl, C$_5$-C$_{10}$ cycloalkyl, phenyl or naphthyl, C$_1$-C$_{15}$ phenylalkyl, or two R$_{22}$ when attached to an N or Si atom can form together with the atom to which they are bonded a pyrrolidine, piperidine or morpholine ring;
R$_{23}$ is hydrogen, OR$_{22}$, NHR$_{22}$, N(R$_{22}$)$_2$ or has the same meaning as R$_{22}$,
R$_{24}$ is OR$_{22}$, NHR$_{22}$, N(R$_{22}$)$_2$ or has the same meaning as R$_{22}$,
R$_{25}$ is hydrogen, OH, OR$_{22}$, NHR$_{22}$ or N(R$_{22}$)$_2$, or has the same meaning as R$_{22}$,
R$_{26}$ is OH, OR$_{22}$, NHR$_{22}$ or N(R$_{22}$)$_2$,
R$_{27}$ is NH$_2$, NHR$_{22}$ or N(R$_{22}$)$_2$,
R$_{28}$ is OH or OR$_{22}$,
R$_{29}$ is C$_1$ or OR$_{22}$,
R$_{30}$ is straight or branched chain C$_1$-C$_{18}$ alkyl; or
R$_{101}$ can be a bridging group of straight or branched C$_1$-C$_{18}$alkylene, C$_6$-C$_{10}$cycloalkylene, para-phenylene or a group

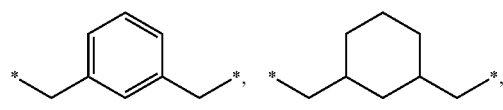

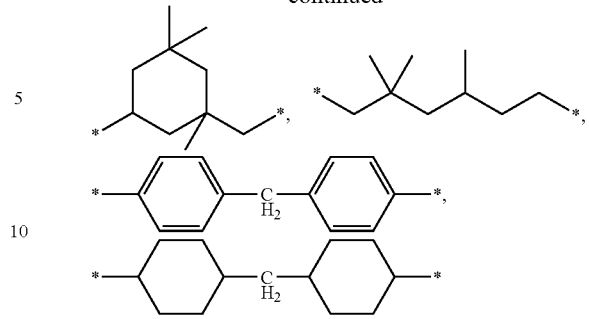

wherein * denotes a bond where the bridge connects two compounds of formula I, said C$_1$-C$_{12}$alkylene, C$_6$-C$_{10}$cycloalkylene can also be interrupted by one or more —O—, —S—, —NH— or —NR$_{22}$— groups or combinations thereof;

or when Y is a direct bond, Z can additionally also be a direct bond;

R$_{102}$ is hydrogen, —CN, —COR$_{24}$ straight or branched chain C$_1$-C$_{24}$alkyl, straight or branched chain C$_2$-C$_{18}$alkenyl, C$_2$-C$_6$alkylnyl, C$_5$-C$_{12}$cycloalkyl, phenyl, naphthyl or C$_7$-C$_{15}$phenylalkyl; or if two substituents R$_{101}$/R$_{102}$ or R$_{102}$/R$_{102}$ are in vicinal position, they can form together with the atoms to which they are bonded an aliphatic, 5 to 8-membered ring;

R$_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or R$_1$ is a group

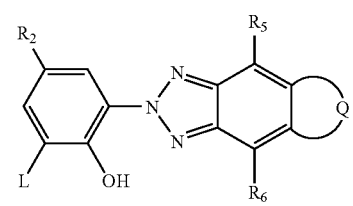

wherein
L is alkylene of 1 to 12 carbon atoms, alkylidene of 2 to 12 carbon atoms, benzylidene, p-xylylene or cycloalkylene of 5 to 7 carbon atoms;
R$_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or
said alkyl substituted by one or more —OH, —OCO—R$_{11}$, —OR$_{14}$, —NCO or —NH$_2$ groups or mixtures thereof, or
said alkyl or said alkenyl interrupted by one or more —O—, —NH— or —NR$_{14}$— groups or mixtures thereof and which can be unsubstituted or substituted by one or more —OH, —OR$_{14}$ or —NH$_2$ groups or mixtures thereof; where
R$_{11}$ is hydrogen, straight or branched chain C$_1$-C$_{18}$alkyl, C$_8$-C$_{12}$cycloalkyl, straight or branched chain C$_3$-C$_8$alkenyl, phenyl, naphthyl or C$_7$-C$_{15}$phenylalkyl; and $R_{14}$ is hydrogen, straight or branched chain alkyl of 1 to 24 carbon atoms; or $R_2$ is —$OR_{14}$, a group —C(O)—O—$R_{14}$, —C(O)—$NHR_{14}$ or —C(O)—$NR_{14}R'_{14}$ wherein $R'_{14}$ has the same meaning as $R_{14}$; or $R_2$ is —$SR_{13}$, —$NHR_{13}$ or —$N(R_{13})_2$; or $R_2$ is —$(CH_2)_m$—CO—$X_1$—$(Z)_p$—Y—$R_{15}$ wherein
$X_1$ is —O— or —$N(R_{16})$—,
Y is —O— or —$N(R_{17})$— or a direct bond,
Z is $C_2$-$C_{12}$-alkylene, $C_4$-$C_{12}$alkylene interrupted by one to three nitrogen atoms, oxygen atoms or a mixture thereof, or is $C_3$-$C_{12}$alkylene, butenylene, butynylene, cyclohexylene or phenylene, each of which may be additionally substituted by a hydroxyl group; or a group

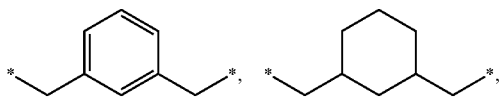

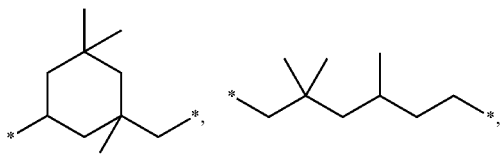

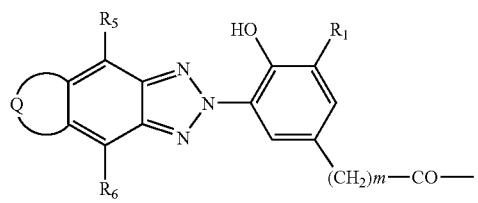

wherein * denotes a bond
or when Y is a direct bond, Z can additionally also be a direct bond;
m is zero, 1 or 2,
p is 1, or p is also zero when X and Y are —$N(R_{16})$— and —$N(R_{17})$—, respectively,
$R_{15}$ is hydrogen, $C_1$-$C_{12}$alkyl, a group

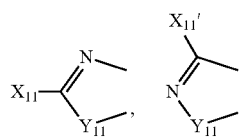

or a group —CO—$C(R_{18})$=C(H)$R_{19}$ or, when Y is —$N(R_{17})$—, forms together with $R_{17}$ a group —CO—CH=CH—CO— wherein $R_{18}$ is hydrogen or methyl, and $R_{19}$ is hydrogen, methyl or —CO—$X_1$—$R_{20}$, wherein
$R_{20}$ is hydrogen, $C_1$-$C_{12}$alkyl or a group of formulae

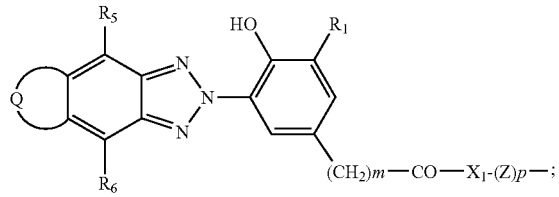

$R_5$ and $R_6$ are independently hydrogen or $C_1$-$C_{18}$alkylene;

$R_{13}$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, phenyl or naphthyl, which both may be substituted by one or two alkyl of 1 to 4 carbon atoms;

$R_{16}$ and $R_{17}$ independently of one another are hydrogen, $C_1$-$C_{12}$-alkyl, $C_3$-$C_{12}$-alkyl interrupted by 1 to 3 oxygen atoms, or is cyclohexyl or $C_7$-$C_{15}$phenylalkyl, and $R_{16}$ together with $R_{17}$ in the case where Z is ethylene, also forms ethylene, wherein a large shift of the absorption maximum of approximately 20-40 nm is observed, when benzo ring of benzotriazole compound of formula (I) or formula (IV) is part of a heterocyclic system.

2. The compound of formula (I) according to claim 1, wherein Q is

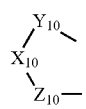

$Y_{10}$ is $NR_{101}$
$X_{10}$ is O=C, S=C, $R_{101}$N;
$Z_{10}$ is O=C, S=C, $R_{101}$N, O, $S(O)_n$ where n is 0;
or $Y_{10}$ is O
$X_{10}$ is O=C, S=C;
$Z_{10}$ is $R_{101}$N;
or $Y_{10}$ is S
$X_{10}$ is O=C, S=C;
$Z_{10}$ is $R_{101}$N;
or Q is $X_{11}$ is $R_{101}$, $N(R_{101})_2$, $S(O)_nR_{101}$ where n is 0;
$X_{11}'$ is $R_{101}$, $N(R_{101})_2$, $S(O)_nR_{101}$ where n is 0;
$Y_{11}$ is C=O, $NR_{101}$, O, or $S(O)_n$ where n is 0;
or Q is

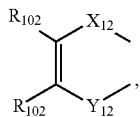

$X_{12}$ is C=O;
$Y_{12}$ is $NR_{101}$, O or S;
or Q is

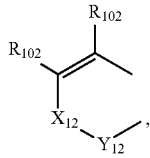

$X_{12}$ is C=O;
$Y_{12}$ is $NR_{101}$, O or S;
or Q is

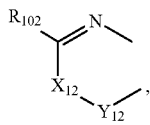

$X_{12}$ is C=O;
$Y_{12}$ is $NR_{101}$ or O;
or Q is

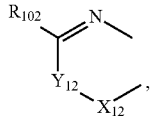

$X_{12}$ is C=O;
$Y_{12}$ is $NR_{101}$ or O;
or Q is

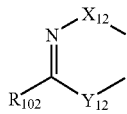

$X_{12}$ is C=O;
$Y_{12}$ is $NR_{101}$ or O;
or Q is

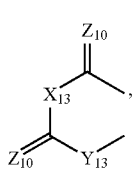

$X_{13}$ is $NR_{101}$, O or S;
$Y_{13}$ is $NR_{101}$;
$Z_{10}$ is O;

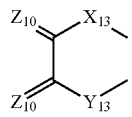

or Q is
$X_{13}$ is $NR_{101}$;
$Y_{13}$ is $NR_{101}$;
$Z_{10}$ is O;
$R_{101}$ is hydrogen, straight or branched chain $C_1$-$C_{24}$alkyl, straight or branched chain $C_2$-$C_{18}$alkenyl, $C_2$-$C_6$ alkinyl, $C_5$-$C_{12}$cycloalkyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more -halogen, —OH, —$OR_{22}$, —$NH_2$, —$NHR_{22}$, —$N(R_{22})_2$, —$NHCOR_{23}$, —$NR_{22}COR_{23}$, —$OCOR_{24}$, —$COR_{25}$, —$SO_2R_{26}$, —$SO_3^-M^+$, —$PO(R_{27})_n(R_{28})_{2-n}$, —$Si(R_{29})_n(R_{30})_{3-n}$, —$Si(R_{22})_3$, —$N^+(R_{22})_3$ $A^-$, —$S^+(R_{22})_2$ $A^-$ or combinations thereof; said straight or branched chain unsubstituted or substituted $C_1$-$C_{24}$ alkyl, straight or branched chain unsubstituted or substituted $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;
said phenyl, naphthyl or $C_7$-$C_{15}$phenylalkyl can also be substituted by one or more -halogen, —CN, —$CF_3$, —$NO_2$, —$NHR_{22}$, —$N(R_{22})_2$, —$SO_2R_{26}$, —$PO(R_{27})_n(R_{28})_{2-n}$, —OH, —$OR_{22}$, —$COR_{25}$, —$R_{25}$; wherein n is 0, 1 or 2;
$R_{22}$ is straight or branched chain $C_1$-$C_{18}$ alkyl, straight or branched chain $C_2$-$C_{18}$alkenyl, $C_5$-$C_{10}$ cycloalkyl, phenyl or naphthyl, $C_7$-$C_{15}$ phenylalkyl, or two $R_{22}$ when attached to an N or Si atom can form together with the atom to which they are bonded a pyrrolidine, piperidine or morpholine ring;
$R_{23}$ is hydrogen, $OR_{22}$, $NHR_{22}$, $N(R_{22})_2$ or has the same meaning as $R_{22}$,
$R_{24}$ is $OR_{22}$, $NHR_{22}$, $N(R_{22})_2$ or has the same meaning as $R_{22}$,
$R_{25}$ is hydrogen, OH, $OR_{22}$, $NHR_{22}$ or $N(R_{22})_2$, or has the same meaning as $R_{22}$,
$R_{26}$ is OH, $OR_{22}$, $NHR_{22}$ or $N(R_{22})_2$,
$R_{27}$ is $NH_2$, $NHR_{22}$ or $N(R_{22})_2$,
$R_{28}$ is OH or $OR_{22}$,
$R_{29}$ is $C_1$ or $OR_{22}$,
$R_{30}$ is straight or branched chain $C_1$-$C_{18}$ alkyl; and
$R_{102}$ is hydrogen, —CN, —$COR_{24}$ straight or branched chain $C_1$-$C_{24}$alkyl, straight or branched chain $C_2$-$C_{18}$alkenyl, $C_2$-$C_6$alkyinyl, $C_5$-$C_{12}$cycloalkyl, phenyl, naphthyl or $C_7$-$C_{15}$phenylalkyl.

3. The compound of formula (I) according to claim 2, wherein Q is

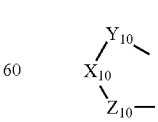

$Y_{10}$ is $NR_{101}$
$X_{10}$ is O=C, S=C
$Z_{10}$ is O=C, $R_{101}$N, O, $S(O)_n$ where n is 0;
or $Y_{10}$ is $NR_{101}$
$X_{10}$ is $NR_{101}$
$Z_{10}$ is O=C;
or Q is

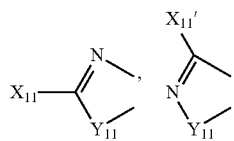

$X_{11}$ is $R_{101}$;
$X_{11}'$ is $R_{101}$;
$Y_{11}$ is C=O, $NR_{101}$, O, or $S(O)_n$ where n is 0;
or Q is

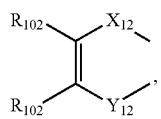

$X_{12}$ is C=O;
$Y_{12}$ is $NR_{101}$ or O;
or Q is

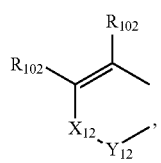

$X_{12}$ is C=O;
$Y_{12}$ is $NR_{101}$ or O;
or Q is

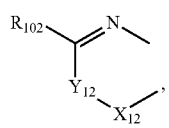

$X_{12}$ is C=O;
$Y_{12}$ is $NR_{101}$ or O;
or Q is

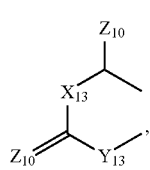

$X_{13}$ is $NR_{101}$;
$Y_{13}$ is $NR_{101}$;
$Z_{10}$ is O;
or Q is

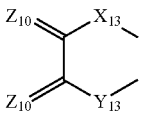

$X_{13}$ is $NR_{101}$;
$Y_{13}$ is $NR_{101}$;
$Z_{10}$ is O;
$R_{101}$ is hydrogen, straight or branched chain $C_1$-$C_{24}$alkyl, straight or branched chain $C_2$-$C_{18}$alkenyl, $C_2$-$C_6$ alkinyl, $C_5$-$C_{12}$cycloalkyl, phenyl, naphthyl or $C_7$-$C_{15}$phenylalkyl; said straight or branched chain said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more —OH; or can also be interrupted by one or more —O—, —S—, —NH— or —$NR_{22}$— groups or combinations thereof;
$R_{22}$ is straight or branched chain $C_1$-$C_{18}$ alkyl, straight or branched chain $C_2$-$C_{18}$ alkenyl, $C_5$-$C_{10}$ cycloalkyl, phenyl or naphthyl or $C_7$-$C_{15}$ phenylalkyl;
$R_{102}$ is hydrogen, —CN, —$COR_{24}$ straight or branched chain $C_1$-$C_{24}$alkyl, straight or branched chain $C_2$-$C_{18}$alkenyl, $C_2$-$C_6$alkylnyl, $C_5$-$C_{12}$cycloalkyl, phenyl, naphthyl or $C_7$-$C_{15}$phenylalkyl; and
$R_{24}$ is $OR_{22}$, $NHR_{22}$, $N(R_{22})_2$ or has the same meaning as $R_{22}$.

4. The compound of formula (I) according to claim 1, wherein
$R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or
$R_1$ is a group

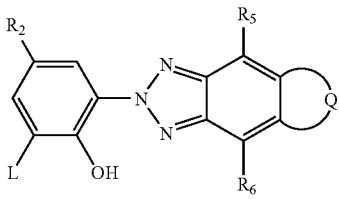

wherein L is alkylene of 1 to 12 carbon atoms, alkylidene of 2 to 12 carbon atoms, benzylidene, p-xylylene or cycloalkylene of 5 to 7 carbon atoms;
$R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or
$R_2$ is —$(CH_2)_m$—CO—$X_1$—$(Z)_p$—Y—$R_{15}$ wherein
$X_i$ is —O—,
Y is —O— or a direct bond,
Z is $C_2$-$C_{12}$-alkylene, $C_4$-$C_{12}$alkylene interrupted by one to three nitrogen atoms, oxygen atoms or a mixture thereof, or when Y is a direct bond, Z can additionally also be a direct bond;

m is 2,
p is 1,
R$_{15}$ is hydrogen, C$_1$-C$_{12}$alkyl or a group

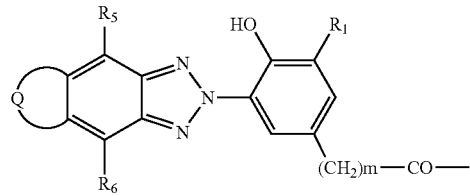

R$_5$ and R$_6$ are independently hydrogen or C$_1$-C$_4$alkyl.

5. The compound of formula (I) according to claim 1, wherein
R$_1$ is hydrogen, straight or branched chain alkyl of 1 to 12 carbon atoms or phenylalkyl of 7 to 15 carbon atoms;
R$_2$ is straight or branched chain alkyl of 1 to 12 carbon atoms or phenylalkyl of 7 to 15 carbon atoms, phenyl, or said phenyl or said phenylalkyl substituted on the phenyl ring by 1 to 3 alkyl of 1 to 4 carbon atoms;
R$_5$ and R$_6$ are hydrogen or C$_1$-C$_4$alkyl.

6. The compound of formula (I) according to claim 1, wherein the compound of formula (I) is a compound according to formulae (a) to (i)

(a)
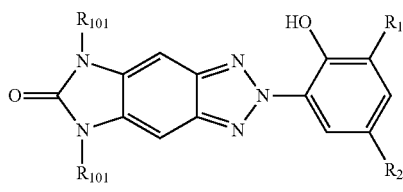

(b)
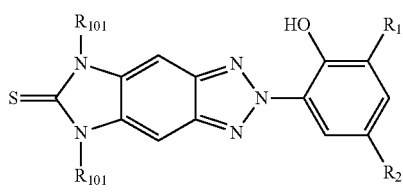

(c)
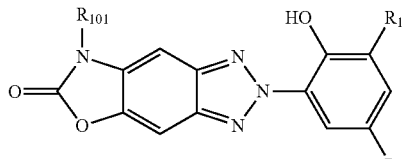

(d)
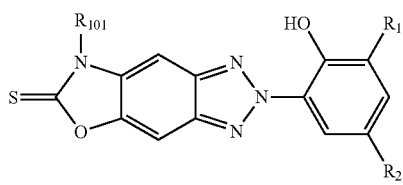

(e)
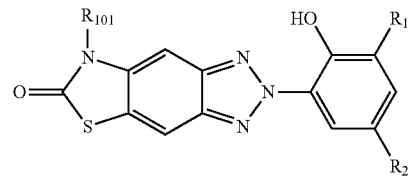

(f)
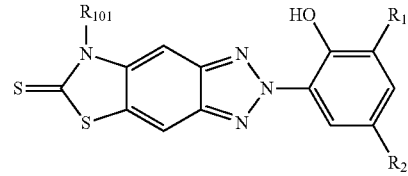

(g)
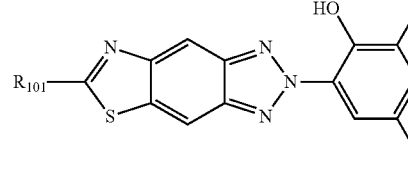

(h)
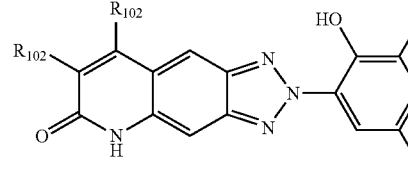

(i)
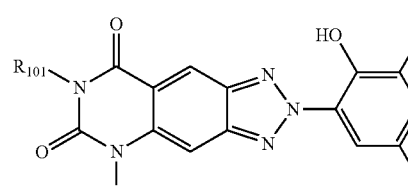

or is

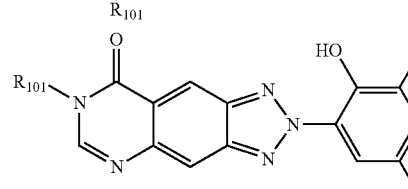

or

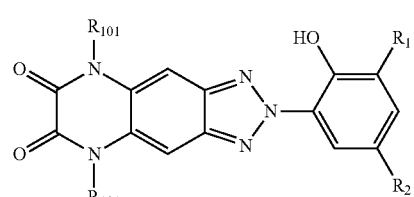

wherein
R$_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms;
R$_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $R_2$ is —$(CH_2)_m$—CO—$X_1$—$(Z)_p$—Y—$R_{15}$ wherein
 $X_1$ is —O—,
 Y is —O— or a direct bond,
 Z is $C_2$-$C_{12}$-alkylene, $C_4$-$C_{12}$alkylene interrupted by one to three nitrogen atoms, oxygen atoms or a mixture thereof, or when Y is a direct bond, Z can additionally also be a direct bond;
 m is 2,
 p is 1,
 $R_{15}$ is hydrogen, $C_1$-$C_{12}$alkyl;
$R_5$ and $R_6$ are hydrogen;
$R_{101}$ is hydrogen, straight or branched chain $C_1$-$C_{24}$alkyl, straight or branched chain $C_2$-$C_{18}$alkenyl, $C_2$-$C_6$ alkinyl, $C_5$-$C_{12}$cycloalkyl, phenyl, naphthyl or $C_7$-$C_{15}$phenylalkyl; said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more —OH; or said straight or branched chain unsubstituted or substituted $C_1$-$C_{24}$ alkyl, straight or branched chain $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;
$R_{22}$ is straight or branched chain $C_1$-$C_{18}$alkyl, straight or branched chain $C_2$-$C_{18}$ alkenyl, $C_5$-$C_{10}$ cycloalkyl, phenyl or naphthyl or $C_7$-$C_{15}$ phenylalkyl;
$R_{102}$ is hydrogen, —CN, —$COR_{24}$ straight or branched chain $C_1$-$C_{24}$alkyl, straight or branched chain $C_2$-$C_{18}$alkenyl, $C_2$-$C_6$alkylnyl, $C_6$-$C_{12}$cycloalkyl, phenyl, naphthyl or $C_7$-$C_{15}$phenylalkyl; and
$R_{24}$ is $OR_{22}$, $NHR_{22}$, $N(R_{22})_2$ or has the same meaning as $R_{22}$.

7. A process for the preparation of a compound of formula (I) according to claim 1

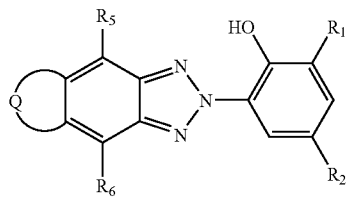

which process comprises reacting a compound of formulae (III)

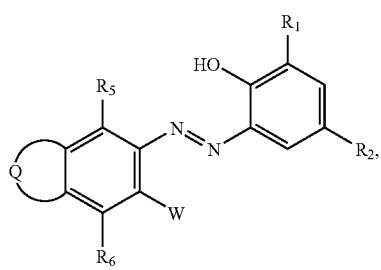

wherein W is halogen or nitro with an azide compound of formula (X)

$$M^{n+}(N_3^-)_r \qquad (X)$$

wherein
M is an n-valent metal cation,

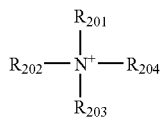

or $P^+(R_{205})_4$,
 $R_{201}$, $R_{202}$, $R_{203}$ and $R_{204}$ are each independently of the others hydrogen or $C_1$-$C_{18}$alkyl,
 $R_{205}$ is $C_1$-$C_{18}$alkyl, and
 r is 1, 2 or 3.

8. The process for the preparation of a compound of formula (I) according to claim 7, wherein the reaction is carried out in a solvent.

9. The process for the preparation of a compound of formula (I) according to claim 7, wherein a molar ratio of the amount of compound of formula III to the amount of azide compound of formula X is from 1:1 to 1:3.

10. The process according to claim 7, wherein the reaction is carried out in the presence of a catalyst.

11. A process for the preparation of a compound of formula (I) according to claim 1

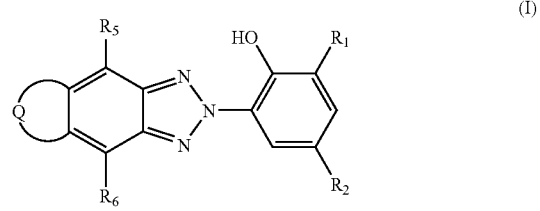

which process comprises reacting a compound of formulae (III)

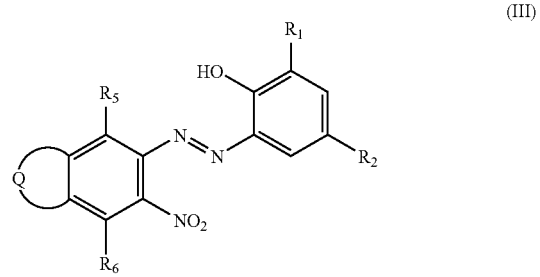

under reductive conditions to a compound of formula (I).

12. A composition stabilized against light-induced degradation which comprises,
 (a) an organic material subject to light-induced degradation, and
 (b) a compound of formula (I) according to claim 1.

13. The composition according to claim 12, which contains additionally a sterically hindered amine stabilizer and/or a UV absorber selected from the group consisting of s-triazines, oxanilides, hydroxybenzophenones, benzoates, a-cyanoacrylates and benzotriazoles different from those of component (b).

14. The composition according to claim 12, wherein the organic material is a recording material.

15. The composition according to claim 12, wherein the organic material is a natural, semi-synthetic or synthetic polymer.

16. The composition according to claim 15, wherein the polymer is a thermoplastic polymer.

17. The composition according to claim 12, wherein the organic material is a coating.

18. The composition according to claim 17, wherein the coating is an automotive coating.

19. The composition according to claim 18, wherein the automotive coating comprises a primer coat which is electrodeposited onto a metal substrate;

at least one pigmented base coat which is in direct contact with the primer coat, containing a compound of component (b); and a clear coat which is in direct contact with the pigmented base coat, containing a UV-absorber selected from the group consisting of the s-triazines, the oxanilides, the hydroxybenzophenones, benzoates, the α-cyanoacrylates and the benzotriazoles different from those of component (b).

20. The composition according to claim 19, which contains in the primer coat a compound of component (b).

21. The composition according to claim 17, wherein the coating is applied over a substrate, which is sensitive to electromagnetic radiation of wavelengths greater than 380 nm.

22. The composition according to claim 12, wherein the compound of formula I is present in an amount of from 0.1% to 30% by weight, based on the weight of the organic material.

* * * * *